(12) United States Patent
Ahamed et al.

(10) Patent No.: US 12,318,088 B2
(45) Date of Patent: Jun. 3, 2025

(54) SURGICAL STAPLING DEVICE WITH RELOADABLE CARTRIDGE

(71) Applicant: Covidien LP, Mansfield, MA (US)

(72) Inventors: Syed Sarfraz Ahamed, Shanghai (CN); Xini Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 236 days.

(21) Appl. No.: 17/907,880

(22) PCT Filed: Feb. 27, 2020

(86) PCT No.: PCT/CN2020/076917
§ 371 (c)(1),
(2) Date: Aug. 29, 2022

(87) PCT Pub. No.: WO2021/168726
PCT Pub. Date: Sep. 2, 2021

(65) Prior Publication Data
US 2023/0113655 A1    Apr. 13, 2023

(51) Int. Cl.
*A61B 17/072* (2006.01)
*A61B 90/00* (2016.01)

(52) U.S. Cl.
CPC .. *A61B 17/072* (2013.01); *A61B 2017/07221* (2013.01); *A61B 2017/07271* (2013.01); *A61B 2017/07285* (2013.01); *A61B 2090/0801* (2016.02)

(58) Field of Classification Search
CPC ........ A61B 17/072; A61B 2017/07221; A61B 2017/07271; A61B 2017/07285
USPC ...................................... 227/175.1
See application file for complete search history.

(56) References Cited

U.S. PATENT DOCUMENTS

| | | | |
|---|---|---|---|
| 1,158,111 | A | 10/1915 | Ahlheim |
| 2,891,250 | A | 6/1959 | Hirata |
| 3,080,564 | A | 3/1963 | Strekopitov et al. |
| 3,252,643 | A | 5/1966 | Strekopov et al. |
| 3,269,630 | A | 8/1966 | Fleischer |
| 3,275,211 | A | 9/1966 | Hirsch et al. |

(Continued)

FOREIGN PATENT DOCUMENTS

| | | |
|---|---|---|
| CN | 102579095 A | 7/2012 |
| CN | 108472037 B | 7/2021 |

(Continued)

OTHER PUBLICATIONS

Snap—definition by Merriam Webster. Accessed from URL https://www.merriam-webster.com/dictionary/snap on Sep. 12, 2024 (Year: 2024).*

(Continued)

*Primary Examiner* — Robert F Long
*Assistant Examiner* — Mary C Hibbert-Copeland

(57) ABSTRACT

A surgical stapling device includes a removable or releasable cartridge assembly. The surgical stapling device and the cartridge assembly include engagement members for releasably securing a thrust bar of the stapling device to a knife assembly of the cartridge assembly. The stapling device also includes structure to prevent the knife assembly from being disengaged from a cartridge body of the cartridge assembly and for obstructing advancement of the knife assembly within the cartridge body after the stapling device has been fired.

19 Claims, 16 Drawing Sheets

(56) References Cited

U.S. PATENT DOCUMENTS

| | | |
|---|---|---|
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,142,066 A * | 2/1979 | Ahamed ............... H04B 14/06 375/247 |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,571,285 A | 11/1996 | Chow et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,828,188 B2 | 11/2010 | Jankowski |
| 7,886,953 B2 | 2/2011 | Schwemberger et al. |
| 8,016,176 B2 | 9/2011 | Kasvikis et al. |
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,328,064 B2 | 12/2012 | Racenet et al. |
| 8,360,296 B2 | 1/2013 | Zingman |

(56) References Cited

U.S. PATENT DOCUMENTS

| | | | |
|---|---|---|---|
| 8,424,738 B2 | 4/2013 | Kasvikis | |
| 8,499,994 B2 | 8/2013 | D'Arcangelo | |
| 8,596,515 B2 | 12/2013 | Okoniewski | |
| 8,627,994 B2 | 1/2014 | Zemlok et al. | |
| 8,646,673 B2 | 2/2014 | Bilotti et al. | |
| 8,757,467 B2 | 6/2014 | Racenet et al. | |
| 8,936,185 B2 | 1/2015 | Racenet et al. | |
| 8,955,732 B2 | 2/2015 | Zemlok et al. | |
| 8,967,446 B2 | 3/2015 | Beardsley et al. | |
| 9,022,273 B1 * | 5/2015 | Marczyk | A61B 17/072 227/176.1 |
| 9,125,651 B2 | 9/2015 | Mandakolathur Vasudevan et al. | |
| 9,192,382 B2 | 11/2015 | Kostrzewski | |
| 9,192,387 B1 | 11/2015 | Holsten et al. | |
| 9,480,474 B2 | 11/2016 | Ji et al. | |
| 9,566,066 B2 | 2/2017 | Kasvikis | |
| 9,579,102 B2 | 2/2017 | Holsten et al. | |
| 9,655,619 B2 | 5/2017 | Zhang et al. | |
| 9,662,111 B2 | 5/2017 | Holsten et al. | |
| 9,668,736 B2 | 6/2017 | Holsten et al. | |
| 9,675,349 B2 | 6/2017 | Holsten et al. | |
| 9,675,350 B2 | 6/2017 | Holsten et al. | |
| 9,675,356 B2 | 6/2017 | Racenet et al. | |
| 9,814,460 B2 | 11/2017 | Kimsey et al. | |
| 9,888,923 B2 | 2/2018 | Chen et al. | |
| 9,962,159 B2 | 5/2018 | Heinrich et al. | |
| 10,004,504 B2 | 6/2018 | Bryant | |
| 10,085,754 B2 | 10/2018 | Sniffin et al. | |
| 10,194,913 B2 | 2/2019 | Nalagatla et al. | |
| 10,939,910 B2 * | 3/2021 | Maddur Shankarsetty | A61B 90/90 |
| 11,666,329 B2 * | 6/2023 | Maddur Shankarsetty | A61B 90/90 227/176.1 |
| 11,826,044 B2 * | 11/2023 | Zhang | A61B 17/072 |
| 2004/0164123 A1 | 8/2004 | Racenet et al. | |
| 2005/0139634 A1 * | 6/2005 | Schwemberger | A61B 17/072 227/19 |
| 2005/0247752 A1 | 11/2005 | Kelly et al. | |
| 2005/0247753 A1 | 11/2005 | Kelly et al. | |
| 2006/0163312 A1 | 7/2006 | Viola et al. | |
| 2007/0187456 A1 | 8/2007 | Viola et al. | |
| 2010/0048988 A1 | 2/2010 | Pastorelli et al. | |
| 2011/0068147 A1 | 3/2011 | Racenet et al. | |
| 2013/0206813 A1 | 8/2013 | Nalagatla | |
| 2016/0249914 A1 | 9/2016 | Zhang et al. | |
| 2016/0249923 A1 | 9/2016 | Hodgkinson et al. | |
| 2016/0270784 A1 | 9/2016 | Wheeler et al. | |
| 2016/0270790 A1 | 9/2016 | Jankowski | |
| 2016/0270793 A1 | 9/2016 | Carter et al. | |
| 2016/0278779 A1 | 9/2016 | Jankowski | |
| 2017/0014134 A1 | 1/2017 | Chen et al. | |
| 2017/0027571 A1 | 2/2017 | Nalagatla et al. | |
| 2017/0027572 A1 * | 2/2017 | Nalagatla | A61B 17/0206 |
| 2017/0027573 A1 | 2/2017 | Nalagatla et al. | |
| 2017/0027574 A1 | 2/2017 | Nalagatla et al. | |
| 2017/0128149 A1 | 5/2017 | Heinrich et al. | |
| 2017/0238923 A1 | 8/2017 | Holsten et al. | |
| 2017/0238924 A1 | 8/2017 | Holsten et al. | |
| 2017/0265861 A1 | 9/2017 | Holsten et al. | |
| 2018/0008261 A1 | 1/2018 | Racenet et al. | |
| 2018/0049739 A1 | 2/2018 | Kasvikis | |
| 2018/0153544 A1 * | 6/2018 | Maddur Shankarsetty | A61B 90/90 |
| 2018/0221024 A1 | 8/2018 | Heinrich et al. | |
| 2019/0000455 A1 * | 1/2019 | Adams | A61B 17/072 |
| 2021/0177409 A1 * | 6/2021 | Maddur Shankarsetty | A61B 90/03 |
| 2022/0249090 A1 * | 8/2022 | Zhang | A61B 17/072 |
| 2023/0113655 A1 * | 4/2023 | Ahamed | A61B 17/072 227/175.1 |
| 2024/0180551 A1 * | 6/2024 | Jin | A61B 17/072 |

FOREIGN PATENT DOCUMENTS

| | | |
|---|---|---|
| EP | 3329862 B1 | 4/2021 |
| JP | 2014133128 A | 7/2014 |

OTHER PUBLICATIONS

Japanese Office Action dated Dec. 27, 2023, issued in corresponding JP Appln. No. 2022551626, 4 pages.

Extended European Search Report dated Feb. 13, 2024, issued in corresponding EP Appln. No. 20921084, 14 pages.

International Search Report for Application No. PCT/CN2020/076917 dated Oct. 26, 2020.

Written Opinion for Application No. PCT/CN2020/076917 dated Oct. 26, 2020.

* cited by examiner

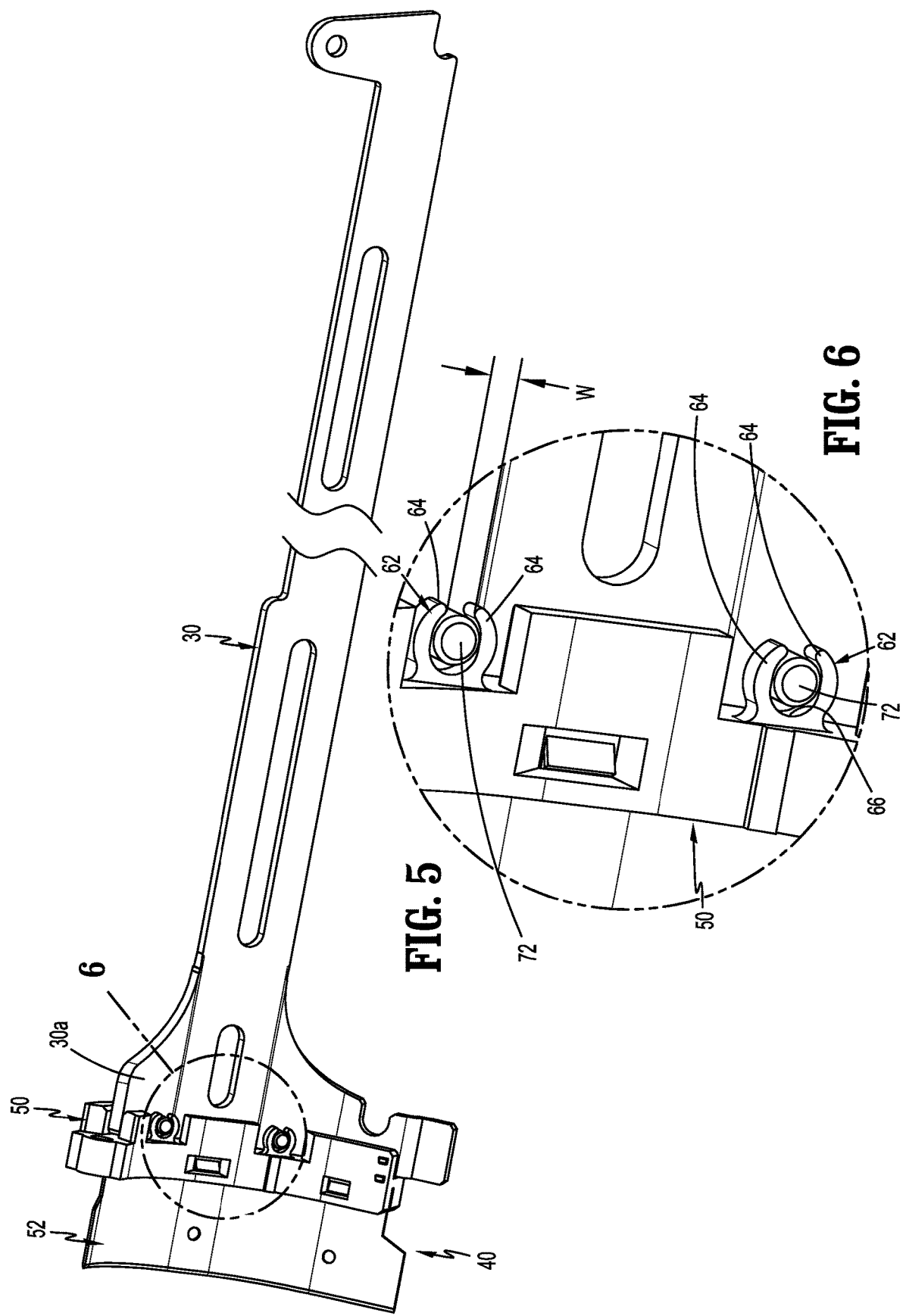

SURGICAL STAPLING DEVICE WITH RELOADABLE CARTRIDGE

FIELD

The technology is generally related to surgical stapling devices and, more particularly, to surgical stapling devices with loadable staple cartridges.

BACKGROUND

Surgical stapling devices for applying rows of staples through compressed living tissue are known in the art and are commonly used for closure of organs during transection or resection procedures and for occlusion of organs during thoracic or abdominal procedures. Such stapling devices include a knife assembly for transecting or resecting the organs simultaneously with the application of rows of staples to the organs.

Typically, stapling devices include a tool assembly including an anvil assembly and a cartridge assembly. The tool assembly is available in a variety of configurations including circular, curved, and linear, and in a variety of orientations including orientations in which the tool assembly is longitudinally aligned with a longitudinal axis of the stapling device and orientations in which the tool assembly is transverse to the longitudinal axis of the stapling device.

Stapling devices with transversely oriented tool assemblies may include a clamp slide mechanism that has a distal portion that receives and supports the cartridge assembly. When the cartridge assembly is loaded onto the clamp slide assembly, it is important that the knife assembly is securely coupled to the stapling device to ensure that the knife assembly can be fully retracted to a position concealed within the cartridge assembly after the stapling device is fired.

SUMMARY

Aspects of this disclosure generally relate to a surgical stapling device including a removable or releasable cartridge assembly. The surgical stapling device and the cartridge assembly include engagement members for releasably securing a thrust bar of the stapling device to a knife assembly of the cartridge assembly. The stapling device also includes structure to prevent the knife assembly from being disengaged from a cartridge body of the cartridge assembly prior to use and for obstructing advancement of the knife assembly after the stapling device has been fired.

One aspect of the disclosure is directed to a stapling device including an elongate body and a tool assembly. The elongate body has a proximal portion and a distal portion and includes a clamp slide assembly and a thrust bar. The clamp slide assembly is movable from a retracted position to an advanced position and includes a distal portion defining a pocket. The thrust bar has a proximal portion and a distal portion and is movable between retracted and advanced positions. The distal portion of the thrust bar includes first engagement members. The tool assembly includes an anvil and a cartridge assembly. The anvil is supported on the distal portion of the elongate body. The cartridge assembly is releasably supported within a pocket of the clamp slide assembly and is movable with the clamp slide assembly in relation to the anvil between retracted and advanced positions. The cartridge assembly includes a cartridge body and a knife assembly. The cartridge body defines a cavity. The knife assembly is movable within the cavity of the cartridge body between retracted and advanced positions and includes a knife holder and a knife blade supported on the knife holder. The knife holder includes a proximal portion having second engagement members. The second engagement members are positioned to engage the first engagement members when the cartridge assembly is supported within the pocket of the clamp slide assembly to secure the knife assembly to the thrust bar.

Other aspects of this disclosure are directed to a cartridge assembly including a cartridge body and a knife assembly. The cartridge body defines a cavity, a proximal cutout, and a distal cutout. The proximal cutout and the distal cutout are longitudinally aligned with each other and the distal cutout has an elongated configuration. The knife assembly is movable within the cavity of the cartridge body between retracted and advanced positions and includes a knife holder and a knife blade supported on the knife holder. The knife holder includes a proximal snap and a distal snap that are longitudinally aligned with each other and with the proximal and distal cutouts in the cartridge body. The proximal snap has a triangular configuration and includes proximal and distal ramped surfaces, and the distal snap has a right-triangular configuration and includes a distal ramped surface and a proximal stop surface. The distal snap is received within the proximal cutout when the knife assembly is in the retracted position prior to firing the stapling device to obstruct proximal movement of the knife assembly from within the cartridge body.

Other aspects of this disclosure are directed to a stapling device including an elongate body and a tool assembly. The elongate body has a proximal portion and a distal portion and includes a clamp slide assembly and a thrust bar. The clamp slide assembly is movable from a retracted position to an advanced position and includes a distal portion defining a pocket. The thrust bar has a proximal portion and a distal portion and is movable between retracted and advanced positions. The distal portion of the thrust bar includes first engagement members. The tool assembly includes an anvil and a cartridge assembly. The anvil is supported on the distal portion of the elongate body. The cartridge assembly is releasably supported within the pocket of the clamp slide assembly and is movable with the clamp slide assembly in relation to the anvil between retracted and advanced positions. The cartridge assembly includes a cartridge body and a knife assembly. The cartridge body defines a cavity, a proximal cutout, and a distal cutout. The proximal cutout and the distal cutout are longitudinally aligned with each other, and the distal cutout has an elongated configuration. The knife assembly is movable within the cavity of the cartridge body between retracted and advanced positions and includes a knife holder and a knife blade supported on the knife holder. The knife holder includes a proximal portion having second engagement members. The second engagement members are positioned to engage the first engagement members when the cartridge assembly is supported within the pocket of the clamp slide assembly to secure the knife assembly to the thrust bar. The knife holder further includes a proximal snap and a distal snap that are longitudinally aligned with each other and with the proximal and distal cutouts in the cartridge body. The proximal snap has a triangular configuration and includes proximal and distal ramped surfaces. The distal snap has a right-triangular configuration and includes a distal ramped surface and a proximal stop surface. The distal snap is received within the proximal cutout when the knife assembly is in the retracted position prior to firing of the stapling device to obstruct proximal movement of the knife assembly from within the cartridge body.

In aspects of the disclosure, the first engagement members and second engagement members are snap-fit together.

In some aspects of the disclosure, the first engagement members include posts secured to the distal portion of the thrust bar and the second engagement members include C-clips secured to the knife holder of the knife assembly.

In certain aspects of the disclosure, each of the C-clips includes resilient arms that define a circular recess and an opening having a width that communicates with the circular recess, and a diameter of the posts is larger than the width of the openings.

In aspects of the disclosure, the knife holder defines a proximally facing channel and spaced cutouts positioned along the proximally facing channel, and the C-clips are positioned on opposite sides of the proximally facing channel within each of the spaced cutouts.

In some aspects of the disclosure, the first engaging members include recesses formed on each side of the distal portion of the thrust bar and the second engagement members include protrusions supported on the knife holder. The protrusions are received within the recesses to secure the knife holder to the thrust bar.

In certain aspects of the disclosure, the knife holder includes spaced resilient walls that support the protrusions.

In aspects of the disclosure, the protrusions are positioned between the spaced resilient walls and the distal portion of the thrust bar is received between the spaced resilient walls.

In some aspects of the disclosure, the cartridge body of the cartridge assembly defines a proximal cutout and a distal cutout that are longitudinally aligned with each other.

In certain aspects of the disclosure, the distal cutout has an elongated configuration.

In aspects of the disclosure, the knife holder of the knife assembly includes a proximal snap and a distal snap that are longitudinally aligned with each other and with the proximal and distal cutouts, and the distal snap is received within the proximal cutout when the knife assembly is in the retracted position prior to firing the stapling device to obstruct proximal movement of the knife assembly from within the cartridge body.

In some aspects of the disclosure, the distal cutout receives the proximal and distal snaps when the knife assembly is in its advanced position.

In certain aspects of the disclosure, the distal snap is received in the distal cutout and the proximal snap is received within the proximal cutout when the knife assembly is in the retracted position after firing of the stapling device. Receipt of the proximal snap within the proximal cutout obstructs distal movement of the knife assembly within the cavity of the cartridge body.

In aspects of the disclosure, the proximal snap has a triangular configuration and includes proximal and distal ramped surfaces, and the distal snap has a right-triangular configuration and includes a distal ramped surface and a proximal stop surface In some aspects of the disclosure, the stapling device includes a handle assembly having a stationary handle and a trigger that is movable in relation to the stationary handle to move the thrust bar between its retracted and advanced positions and to move the clamp slide assembly between its retracted and advanced positions.

In certain aspects of the disclosure, the distal snap is positioned to engage a portion of the cartridge body defining the distal cutout after firing of the stapling device but prior to movement of the thrust bar to its retracted position such that the thrust bar moves to its retracted position independently of the knife holder, such movement of thrust bar independently of the knife holder effecting separation of the first and second engagement members to disengage the thrust bar from the knife holder.

Other features of the disclosure will be appreciated from the following description.

BRIEF DESCRIPTION OF DRAWINGS

Various aspects of the disclosure are described herein below with reference to the drawings, wherein:

FIG. 5 is a side perspective view of the thrust bar and knife assembly of the surgical sapling device shown in FIG. 1 with the knife assembly coupled to the thrust bar;

FIG. 6 is an enlarged view of the indicated area of detail shown in FIG. 5;

DETAILED DESCRIPTION

Figure 1:
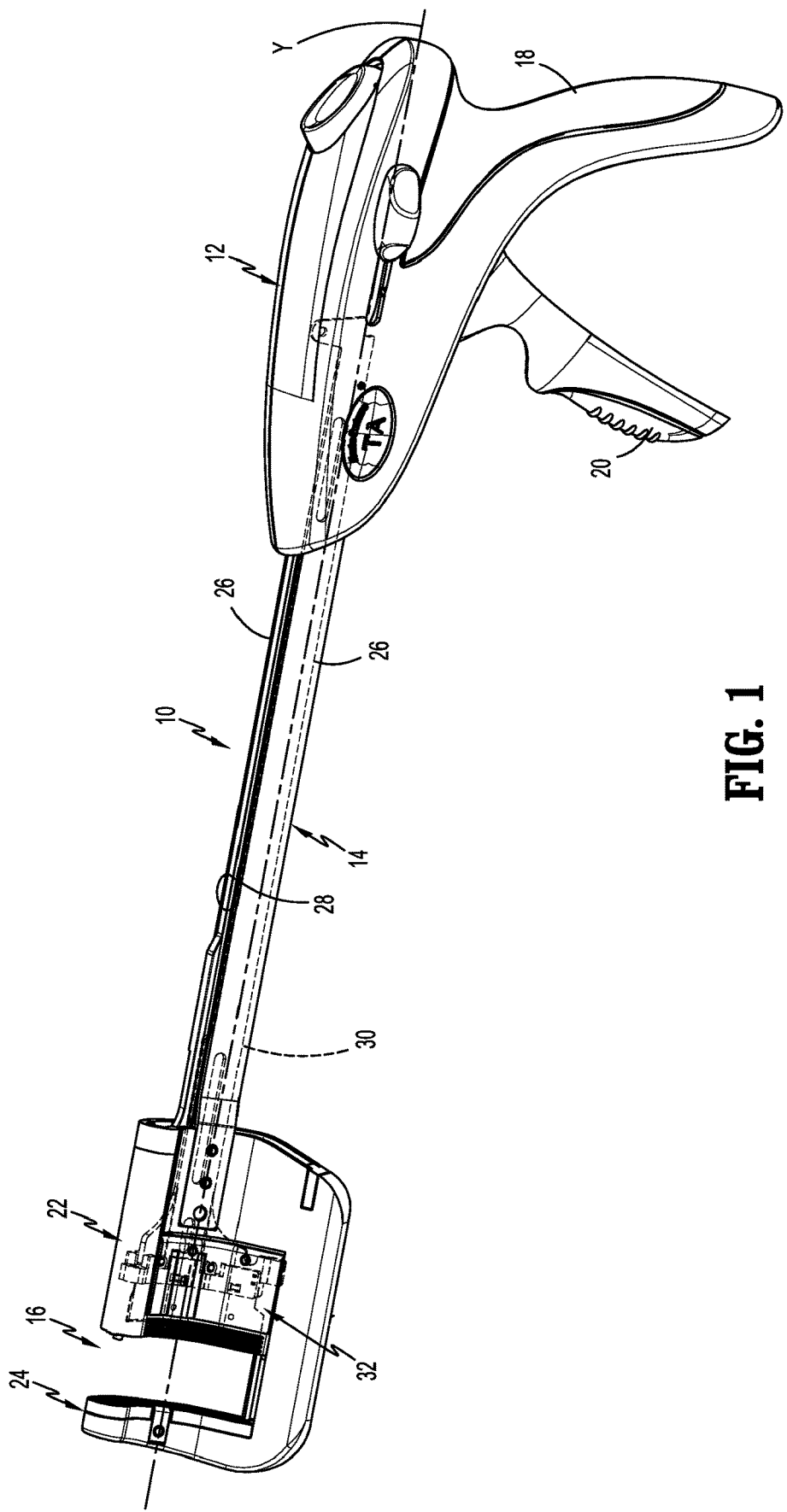
FIG. 1 is a side perspective view of a surgical stapling device including various aspects of the disclosure.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

The disclosed surgical stapling device has a clamp slide assembly and a tool assembly that includes an anvil assembly and a cartridge assembly. The cartridge assembly is releasably supported on the clamp slide assembly to facilitate replacement of the cartridge assembly and reuse of the surgical stapling device. The clamp slide assembly is movable within the surgical stapling device to move the cartridge assembly in relation to the anvil assembly between spaced and clamped positions. The surgical stapling device includes a thrust bar and the cartridge assembly includes a knife assembly that is coupled to the thrust bar when the cartridge assembly is positioned on the clamp slide assembly. The thrust bar and the knife assembly include engagement structure that is configured to secure the knife assembly to the thrust bar to allow the knife assembly to remain engaged with the thrust bar during retraction of the knife assembly but to allow separation of the knife assembly during replacement of the cartridge assembly.

FIG. 1 illustrates the disclosed surgical stapling device shown generally as stapling device 10. The stapling device 10 includes a handle assembly 12, an elongate body 14 that defines a longitudinal axis "Y", and a tool assembly 16. The handle assembly 12 includes a stationary handle 18 and a trigger 20 that is movable in relation to the stationary handle 18 to actuate the tool assembly 16. The tool assembly 16 includes a cartridge assembly 22 and an anvil assembly 24 that define axes that are transverse to the longitudinal axis "Y" of the elongate body 14. The cartridge assembly 22 includes a cartridge body 20a that is supported on a distal end portion of the elongate body 14 and is movable in relation to the anvil assembly 24 between a spaced position (FIG. 1) and a clamped position. In the clamped position, the cartridge assembly 22 is in juxtaposed alignment with the anvil assembly 24. In some aspects of the disclosure, the cartridge assembly 22 and the anvil assembly 24 are curved along their transverse axes to facilitate access to certain anatomical regions of a patient.

Figure 2:
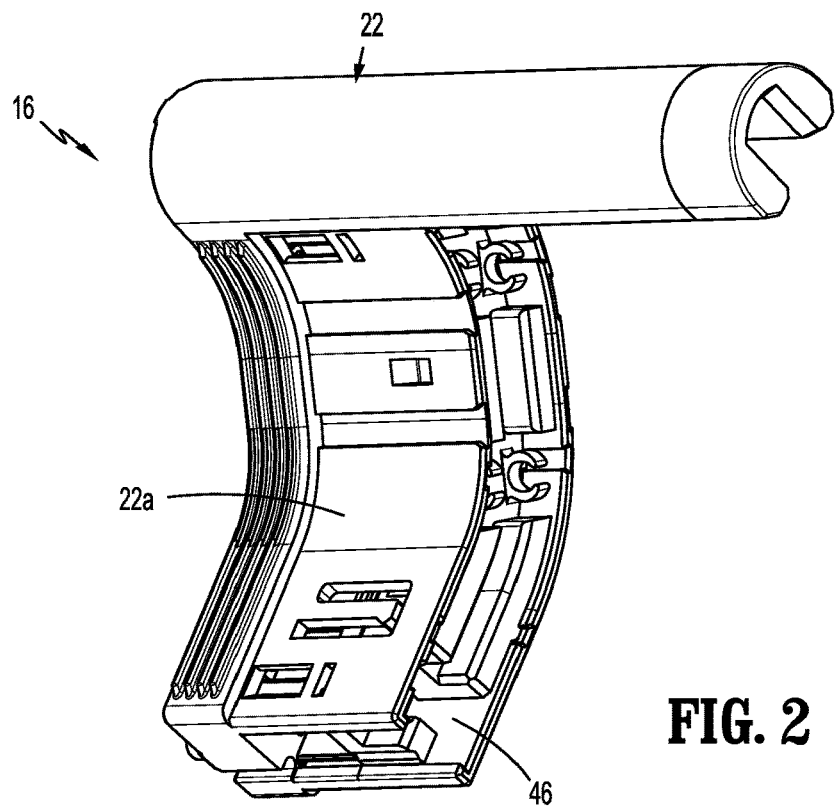
FIG. 2 is a side perspective of a cartridge assembly of the surgical stapling device shown in FIG. 1.

In aspects of the disclosure, the elongate body 14 includes spaced frame members 26 that extend from the handle assembly 12 to the tool assembly 16. The frame members 26 define an elongate channel 28 that receives a thrust bar 30 and a clamp slide assembly 32 (FIG. 2). The clamp slide assembly 32 includes a distal portion 34 (FIG. 2) that defines a curved pocket 36 (FIG. 2) that receives the cartridge assembly 22. The clamp slide assembly 32 can move within the elongate channel 28 defined by the frame members 26 between retracted and advanced positions in response to actuation of the trigger 20 to move the cartridge assembly 22 in relation to the anvil assembly 24 between the spaced position and the clamped position. The thrust bar 30 is movable within the elongate channel 28 between a retracted position and an advanced position, also in response to actuation of the trigger 20, to eject staples from the cartridge assembly 22. U.S. Pat. No. 6,817,508 discloses a surgical stapling device including exemplary aspects of a handle assembly, a clamp slide assembly, and a thrust bar.

Figure 3:
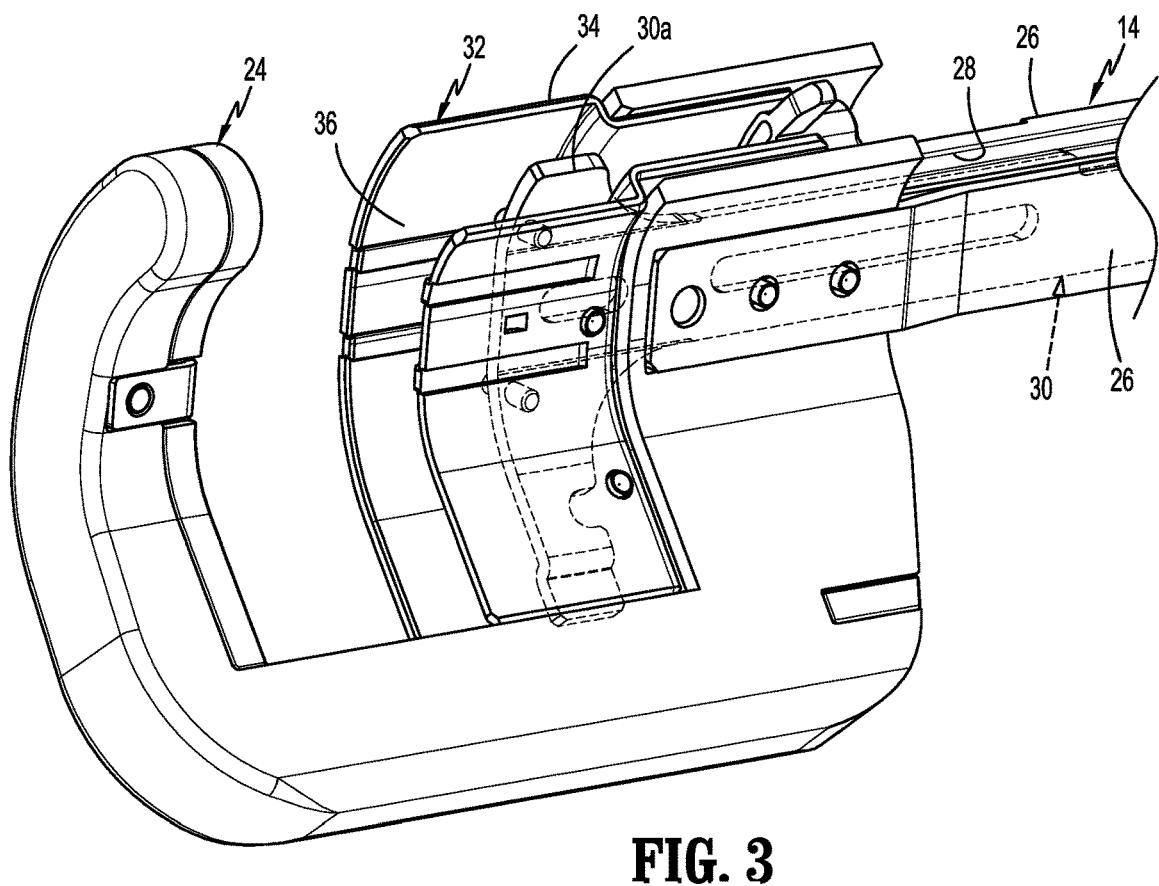
FIG. 3 is a side perspective of a distal portion of the surgical stapling device shown in FIG. 1 with the cartridge assembly removed from tool assembly.

FIGS. 2 and 3 illustrate the distal portion of the surgical stapling device 10 including the tool assembly 16 with the cartridge assembly 22 separated from the clamp slide assembly 32 and the thrust bar 30 and the clamp slide assembly 32 in a retracted position (FIG. 3). As illustrated, the distal portion 30a of the thrust bar 30 is positioned within the curved pocket 36 defined by the clamp slide assembly 32 when the clamp slide assembly 32 and the thrust bar 30 are in their retracted positions.

Figure 4:
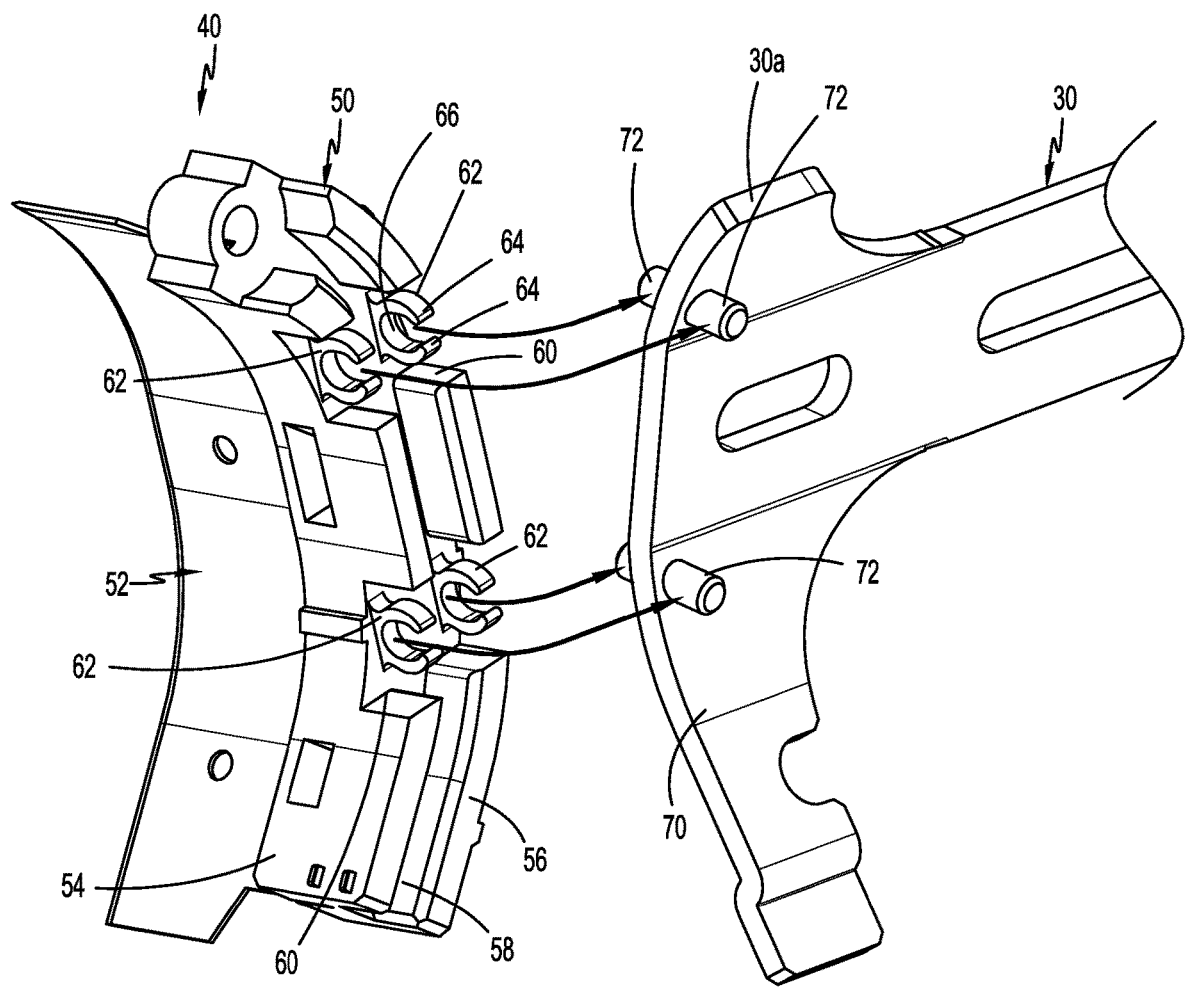
FIG. 4 is a side perspective view of a distal portion of a thrust bar and knife assembly of the surgical stapling device shown in FIG. 1 with the knife assembly separated from the thrust bar.

FIG. 4 illustrates the distal portion 30a of the thrust bar 30 and a knife assembly 40 of the cartridge assembly 22 with the knife assembly 40 separated from the thrust bar 30. The cartridge body 22a (FIG. 2) defines a cavity 46 that receives the knife assembly 40 such that the knife assembly 40 can move from a retracted position to an advanced positon within cavity 46 of the cartridge body 22a.

The knife assembly 40 includes a knife holder 50 and a knife blade 52. The knife holder 50 includes a distal portion 54 and a proximal portion 56. The knife blade 52 is secured to the distal portion 54 of the knife holder 50. The proximal portion 56 of the knife holder 50 defines a proximally facing channel 58 and spaced cutouts 60 positioned adjacent and on opposite sides of the channel 58. The proximal portion 56 of the knife holder 50 includes an engagement member 62 positioned in each of the cutouts 60 on opposite sides of the proximally facing channel 58. In aspects of the disclosure, each of the engagement members 62 forms a C-clip that includes resilient arms 64 that define a circular recess 66.

The distal portion 30a of the thrust bar 30 includes body 70 that supports engagement members 72. In aspects of the disclosure, each of the engagement members 72 on the body 70 of the thrust bar 30 includes posts or pins 72 that extend from sides of the thrust bar 30 and are positioned to be received within the C-clips 62 of the knife holder 50 when cartridge assembly 22 is inserted into the curved pocket 36 on the distal portion 34 of the clamp slide assembly 30.

FIGS. 5 and 6 illustrate the knife holder 50 coupled to the distal portion 30a of the thrust bar 30. In order to secure the cartridge assembly 22 (FIG. 2) to the clamp slide assembly 32 (FIG. 3), the cartridge assembly 32 is first inserted transversely into the curved pocket 36 to a position in which the C-clips 62 of the knife holder 50 are aligned with the posts 72 of the thrust bar 30. When the C-clips 62 are aligned with the posts 72, the cartridge assembly 22 is moved proximally within the curved pocket 36 of the clamp slide assembly 32 towards the thrust bar 30 to move the C-clips 62 of the knife holder 50 into engagement with the posts 72 of the thrust bar 30. As illustrated in FIG. 6, the diameters of the posts 72 are larger than a width "W" of the openings into the C-clips 62. As such, when the C-clips 62 engage the posts 72, the flexible arms 64 of the C-clips 62 flex outwardly to allow the posts 72 to be received within the circular recesses 66 of the C-clips 62. When the posts 72 are received within the circular recesses 66 of the C-clips 62, the flexible arms 64 snap back to their undeformed positions to secure the knife holder 50 to the thrust bar 30. In the assembled configuration, the distal portion 30a of the thrust bar 30 is received within the proximally facing channel 58 of the knife holder 50.

Figure 7:
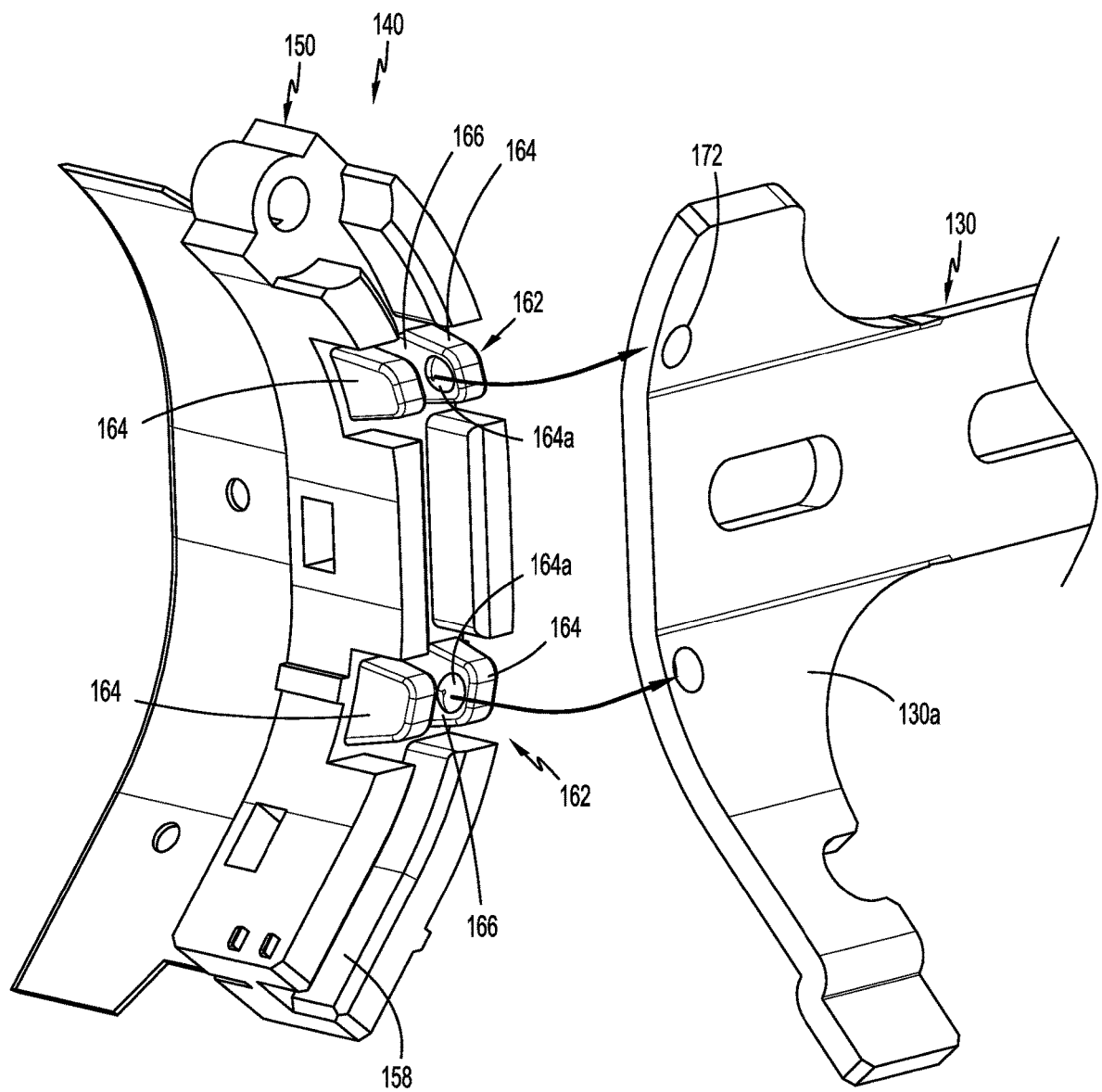
FIG. 7 is a side perspective view of other alternate aspects the knife assembly and thrust bar of the surgical stapling shown in FIG. 1 with the parts separated.
Figure 8:
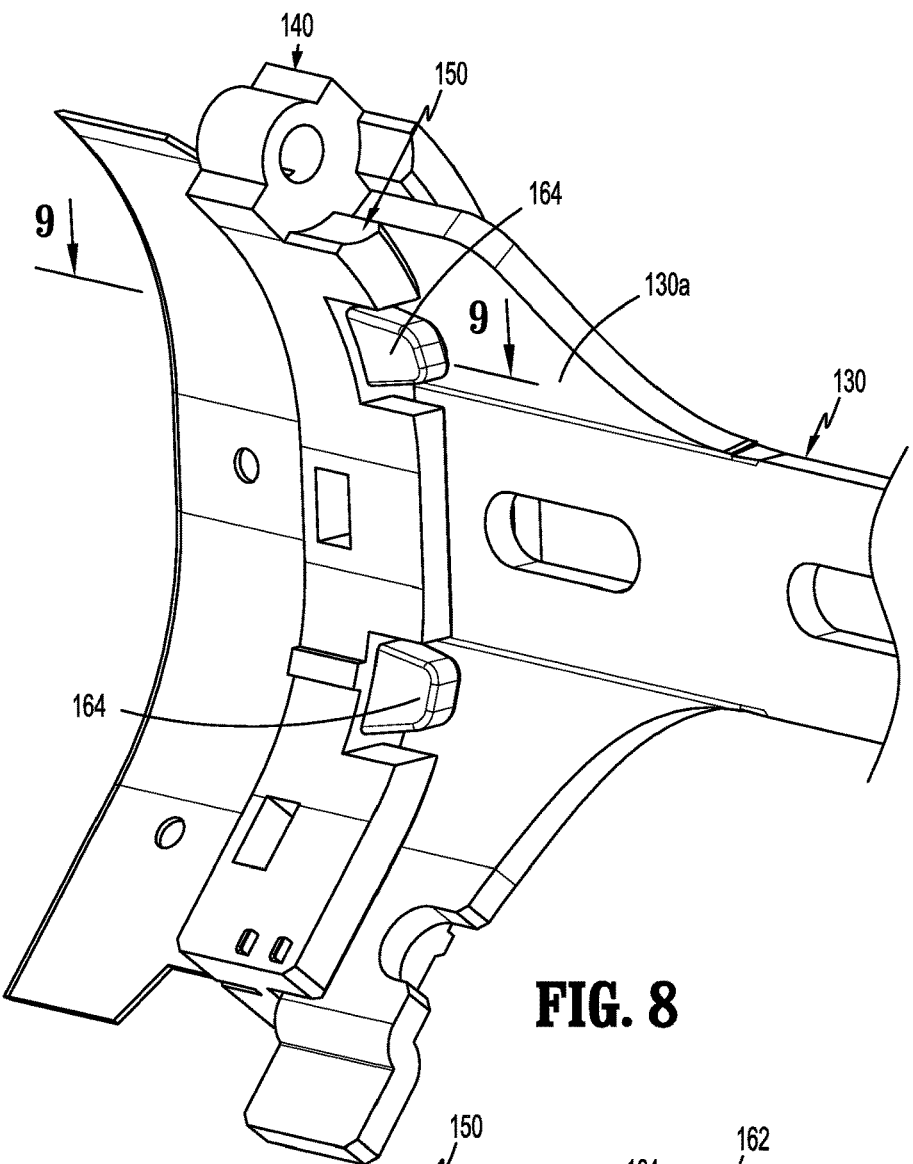
FIG. 8 is a side perspective view of the knife assembly and thrust bar shown in FIG. 7 coupled together.
Figure 9:
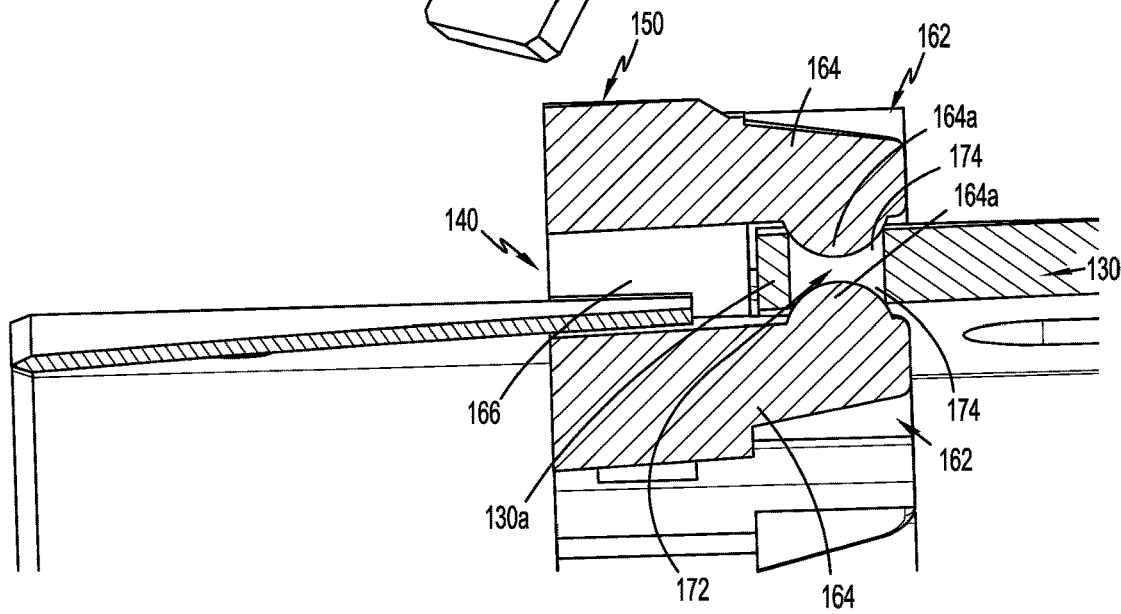
FIG. 9 is a cross-sectional view taken along section line 9-9 of FIG. 8.

FIGS. 7-9 illustrate alternate versions of the knife holder and thrust bar of the stapling device shown in FIG. 1 shown generally as knife holder 150 and thrust bar 130. The knife holder 150 forms part of a knife assembly 140 which is substantially identical to the knife assembly 40 (FIG. 4) except that the engagement members 62 have been modified. More particularly, each of the engagement members 162 on the knife holder 150 includes a pair of spaced resilient walls 164 that define a slot 166 for receiving the distal portion 130a of the thrust bar 130. Each wall 164 of the spaced walls includes a protrusion 164a that projects inwardly from each of the respective walls 164 into the slot 166. In aspects of the disclosure, the protrusions 164a can be spherical in shape although other shapes are envisioned.

The thrust bar 130 is also substantially identical to thrust bar 30 except that the engagement members 72 have been modified. More specifically, the engagement members 172 on the distal portion 130a of the thrust bar 130 include recesses 174 formed on opposite sides of the distal portion of the thrust bar 130. In certain aspects of the disclosure, the recesses 174 on the opposite sides of the thrust bar 130 can be formed by through bores formed in the distal portion 130a of the thrust bar 130. Alternately, the recesses 174 can be formed by diametrically opposed concavities that do not communicate with each other.

The cartridge assembly 22 is secured to the clamp slide assembly 32 in the same manner as described above. More specifically, when the cartridge assembly 22 (FIG. 2) is moved proximally within the curved pocket 36 (FIG. 3) defined by the clamp slide assembly 32, the distal portion 130a of the thrust bar 130 is received in the proximally facing channel 158 (FIG. 7) of the knife holder 150 in a position in which the engagement members 162 of the knife holder 150 are aligned with the engagement members 172 of the thrust bar 130. As the cartridge assembly 122 (FIG. 2) is moved proximally in relation to the thrust bar 130, the distal portion 130a of the thrust bar 130 moves within the slot 166 defined between the resilient walls 164 of the engagement members 162. When the protrusions 164a of the knife holder 150 engage the distal portion 130a of the thrust bar 130, the walls 164 flex outwardly to allow the protrusions 164a to pass over the distal portion 130a of the thrust bar 130 and snap into the recesses 174 formed in the distal portion 130a of the thrust bar 130. Receipt of the protrusions 164a of the knife holder 150 within the recesses 174 of the thrust bar 130 couples the knife holder 150 to the thrust bar 130.

FIGS. 10-16 illustrate an alternate version of the cartridge assembly of the stapling device 10 (FIG. 1) shown generally as cartridge assembly 222. The cartridge assembly 222 includes a knife assembly 240 and a cartridge body 222a. The cartridge assembly 222 and the knife holder 250 include structure to retain the knife assembly 240 within the cartridge body 222a prior to firing of the cartridge assembly 222, and to retain the knife assembly 240 in a retracted position after firing of the cartridge assembly 222 to prevent injury to a clinician.

Figure 10:
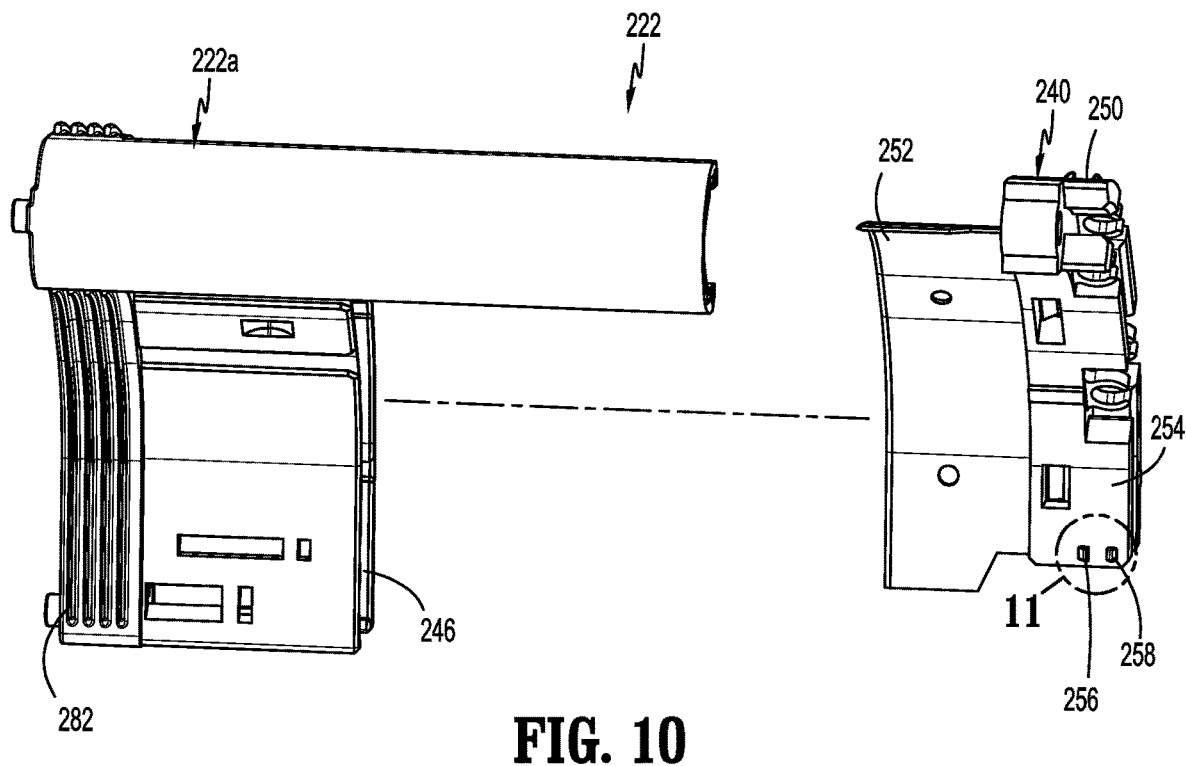
FIG. 10 is a side perspective view of other aspects of the cartridge assembly of the surgical stapling device shown in FIG. 1 with the knife assembly separated from the cartridge body.
Figure 11:
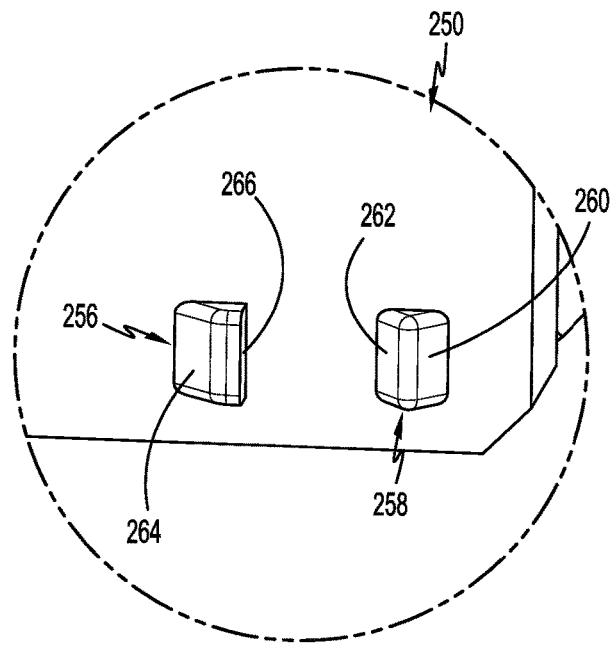
FIG. 11 is an enlarged view of the indicated area of detail shown in FIG. 10.

FIGS. 10 and 11 illustrate perspective views of the cartridge assembly 222 with the knife assembly 240 separated from the cartridge body 222a of the cartridge assembly 222. The knife assembly 240 is substantially as described above in regard to the knife assembly 40 (FIG. 4) and includes a knife holder 250 and a knife blade 252 that is secured to a distal portion of the knife holder 250. The knife holder 250 includes a body 254 that has an outer surface including two longitudinally aligned snaps including a distal snap 256 and a proximal snap 258. In aspects of the disclosure, the proximal snap 258 (FIG. 11) has a triangular configuration and includes a proximal ramped surface 260 and a distal ramped surface 262, and the distal snap 256 (FIG. 11) has a right-triangular configuration and includes a ramped distal surface 264 and a vertical stop surface 266.

The cartridge body 222a defines a cavity 246 that receives the knife assembly 240 such that the knife assembly 240 can move between a retracted position (FIG. 13) and an advanced position (FIG. 14) within the cavity 246 of the cartridge body 22a. The cartridge body 222a defines a proximal cutout 270 and a distal cutout 274 which are longitudinally aligned with each other. The distal cutout 274 defines an elongated slot that is positioned to receive the proximal and distal snaps 258 and 256 simultaneously. The proximal cutout 270 is dimensioned to receive one of the proximal and distal snaps 258 and 256 at one time.

Figure 12:
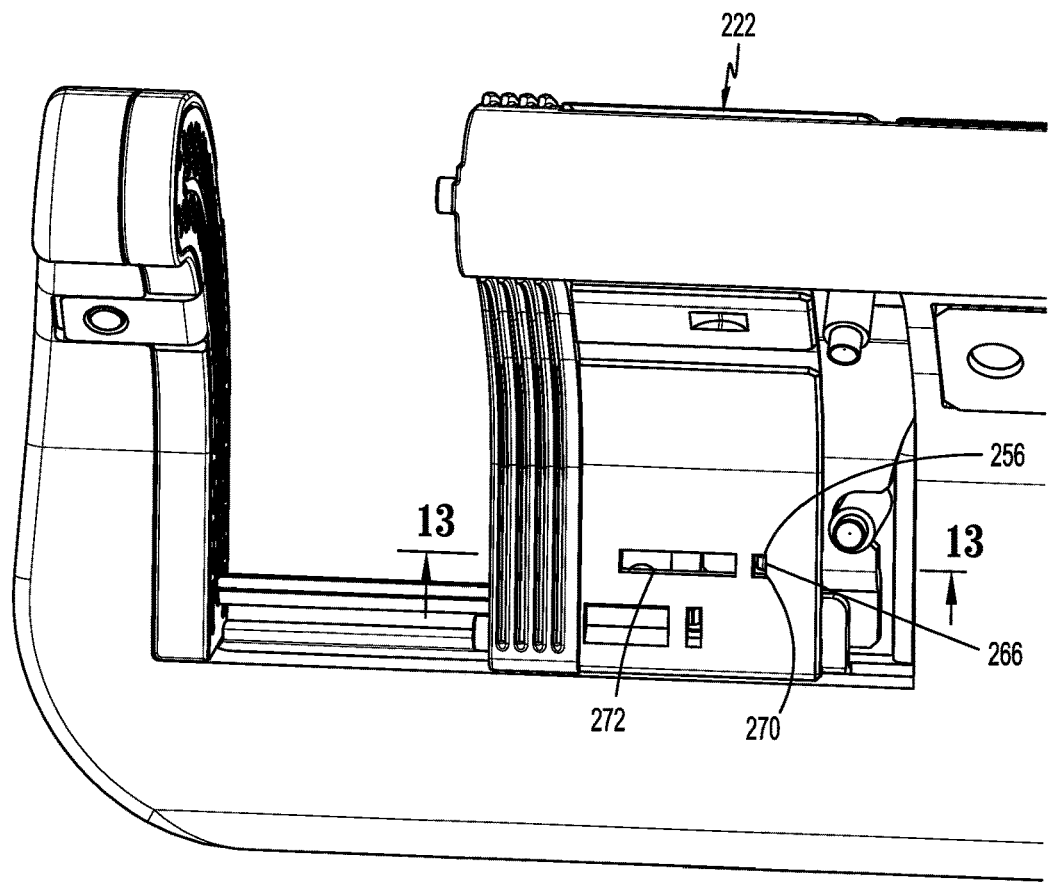
FIG. 12 is a side perspective view of the cartridge assembly shown in FIG. 10 supported on a distal portion of the surgical stapling device shown in FIG. 1 in a pre-fired retracted position.
Figure 13:
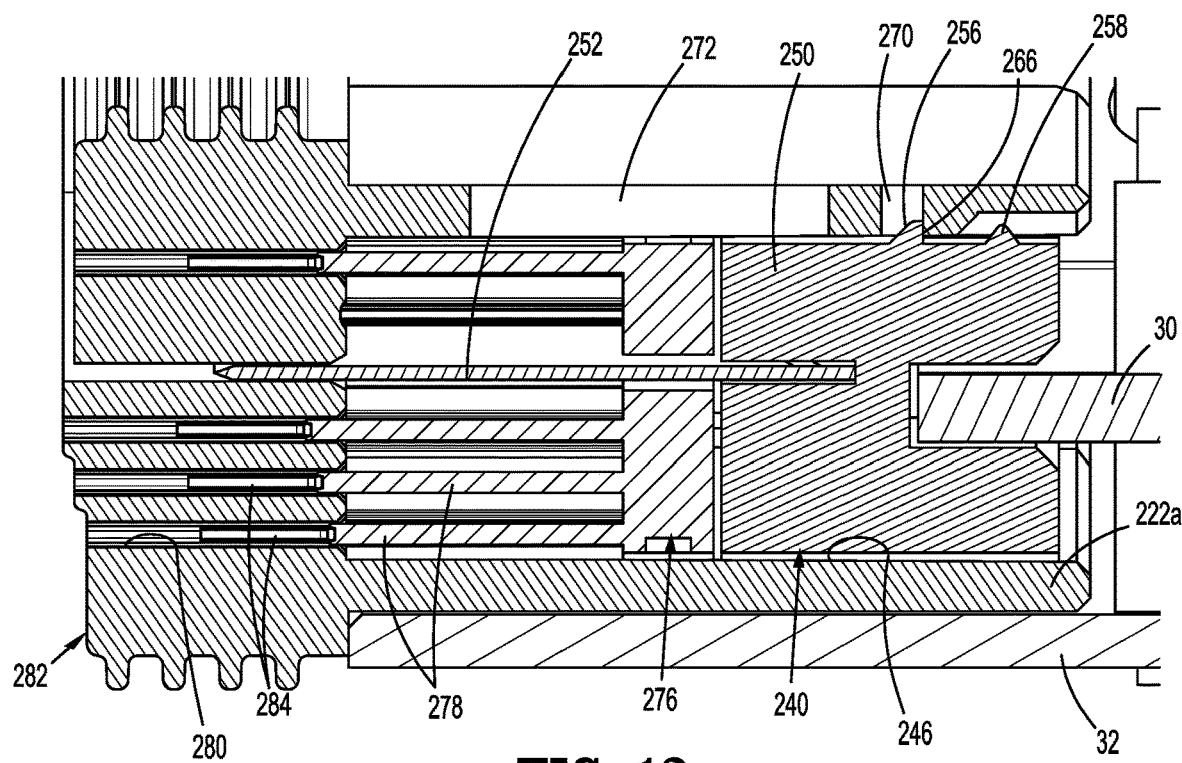
FIG. 13 is a cross-sectional view taken along section line 13-13 of FIG. 12.

FIGS. 12 and 13 illustrate the tool assembly 16 of the stapling device 10 (FIG. 1) with the cartridge assembly 222 in a retracted position pre-fired position. In the pre-fired position, the knife assembly 240 is positioned proximally of a staple pusher 276 within the cavity 246 of the cartridge body 222a. As is known in the stapling arts, the staple pusher 276 includes fingers 278 (FIG. 13) that move through channels 280 defined within a staple cartridge 282 to eject staples 284 from the staple cartridge 282. In the pre-fired position, the distal snap 256 is received within the proximal cutout 270 such that the stop surface 266 on the proximal side of the distal snap 256 engages the cartridge body 222a. Engagement between the stop surface 266 of the distal snap 256 and the cartridge body 222a obstructs proximal movement of the knife assembly 240 within the cavity 246 of the cartridge body 222a to prevent the knife assembly 240 from falling from the cavity 246 of the cartridge body 222a.

Figure 14:
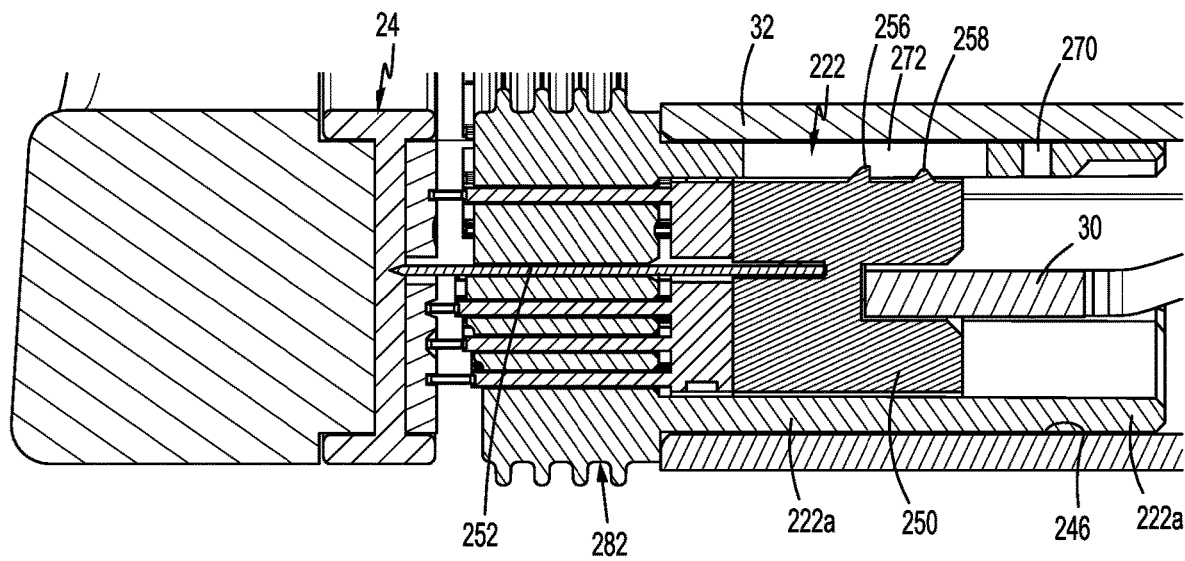
FIG. 14 is a cross-sectional view taken along section line 13-13 of FIG. 12 after the surgical stapling device is moved to a clamped and fired position.

FIG. 14 illustrates the tool assembly 16 of the stapling device 10 with the cartridge assembly 222 in a clamped and fired position. In the clamped and fired position, the staple pusher 276 and the knife assembly 240 are in their advanced positions within the cavity 246 of the cartridge body 222a with the fingers 278 of the staple pusher 276 extending through the channels 280 in the staple cartridge 282 and the knife blade 252 extending into the anvil assembly 24. In this position, the distal and proximal snaps 256 and 258 are both positioned in the elongated cutout 272 formed in the cartridge body 222a of the cartridge assembly 222.

Figure 15:
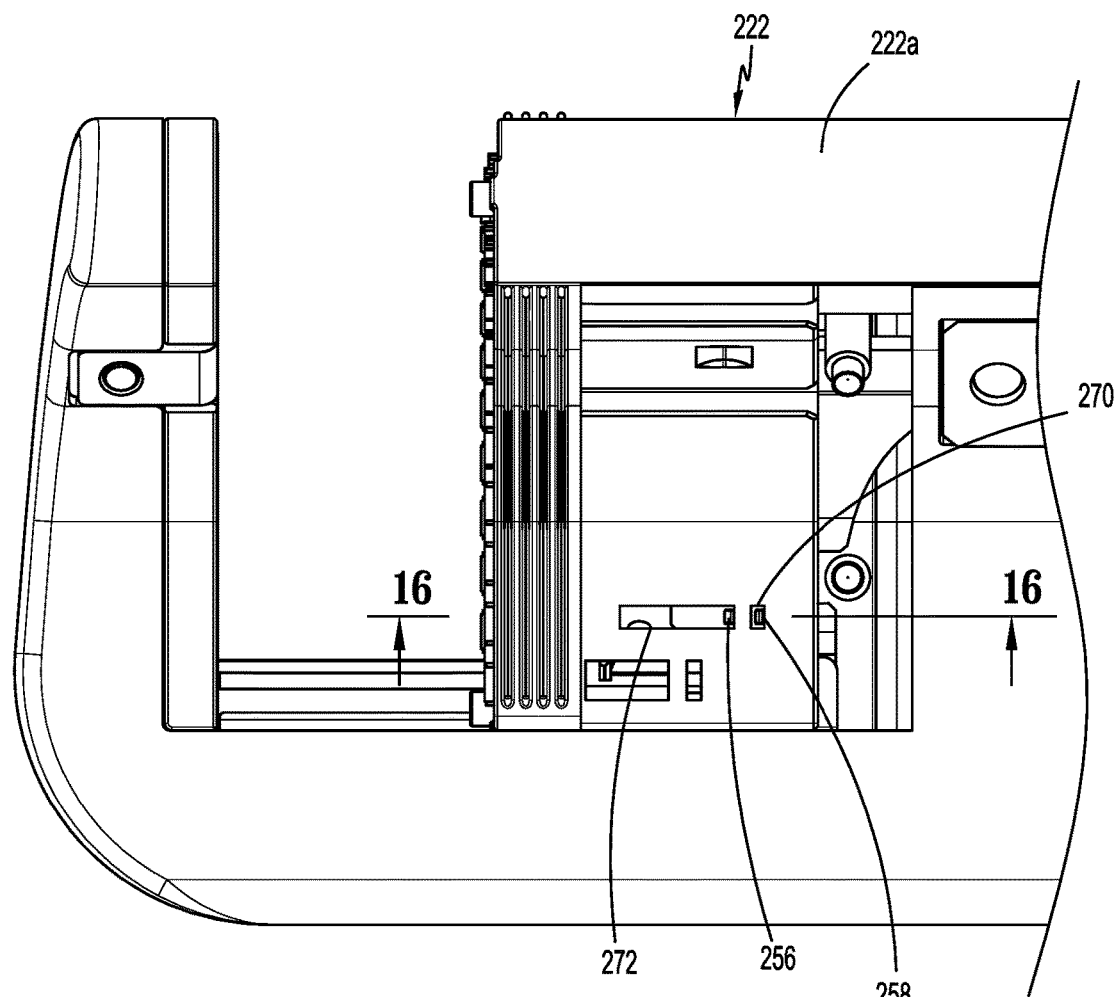
FIG. 15 is a side perspective view of the distal portion of the surgical stapling device shown in FIG. 10 in a retracted position after the surgical stapling device has been fired.
Figure 16:
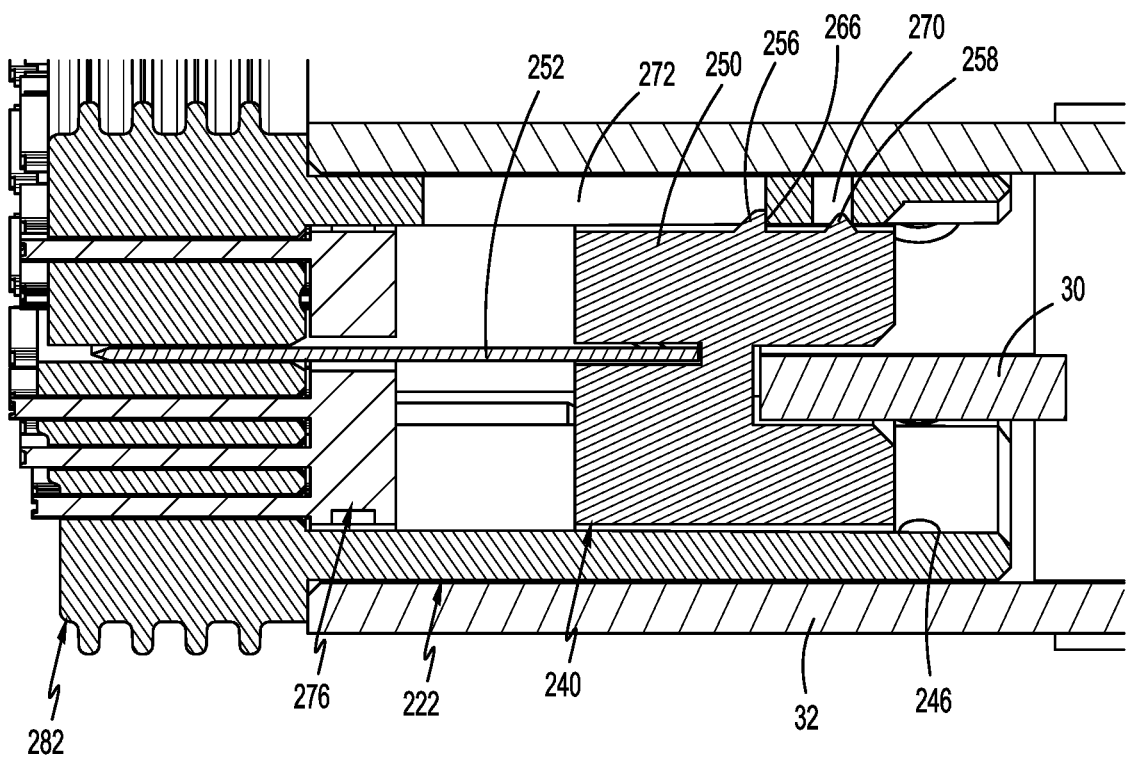
FIG. 16 is a cross-sectional view taken along section line 16-16 of FIG. 15.

FIGS. 15 and 16 illustrate the tool assembly 16 of the stapling device 10 (FIG. 1) after the device 10 is fired and the cartridge assembly 222 is returned to the retracted positon. In this position, the knife assembly 240 is in its retracted position within the cavity 246 of the cartridge body 222a such that the knife blade 252 is recessed within the cartridge body 222a to protect a clinician from injury. The distal snap 256 is positioned in the distal cutout 272 and the proximal snap 258 is positioned in the proximal cutout 270. As discussed above, the stop surface 266 of the distal snap 256 engages the cartridge body 222a to prevent the knife assembly 240 from falling from the proximal end of the cavity 246 defined by the cartridge body 222a. In addition, the proximal snap 258 which is positioned in the proximal cutout 270 obstructs distal movement of the knife assembly 240 within the cavity 246 of the cartridge body 222 to minimize the likelihood that the knife blade 252 moves distally from the cartridge body 222a of the cartridge assembly 222 and becomes exposed to clinician.

It is also noted that the distal snap 256 is positioned to engage the cartridge body 222 prior to full retraction of the thrust bar 30, 130 (FIGS. 4 and 7). As such, the knife assembly 240 will be obstructed from moving proximally as the thrust bar 30, 130 continues to retract. This relative movement between the thrust bar 30, 130 and the knife assembly 240 effects disengagement of the protrusions 164a of the knife holder 150 from the recesses 174 of the thrust bar 130 (or separation of the engagement member 62 of the knife holder 50 and the posts 72 of the thrust bar 30) to facilitate separation of the thrust bar 130 and the knife holder 250.

Figure 17:
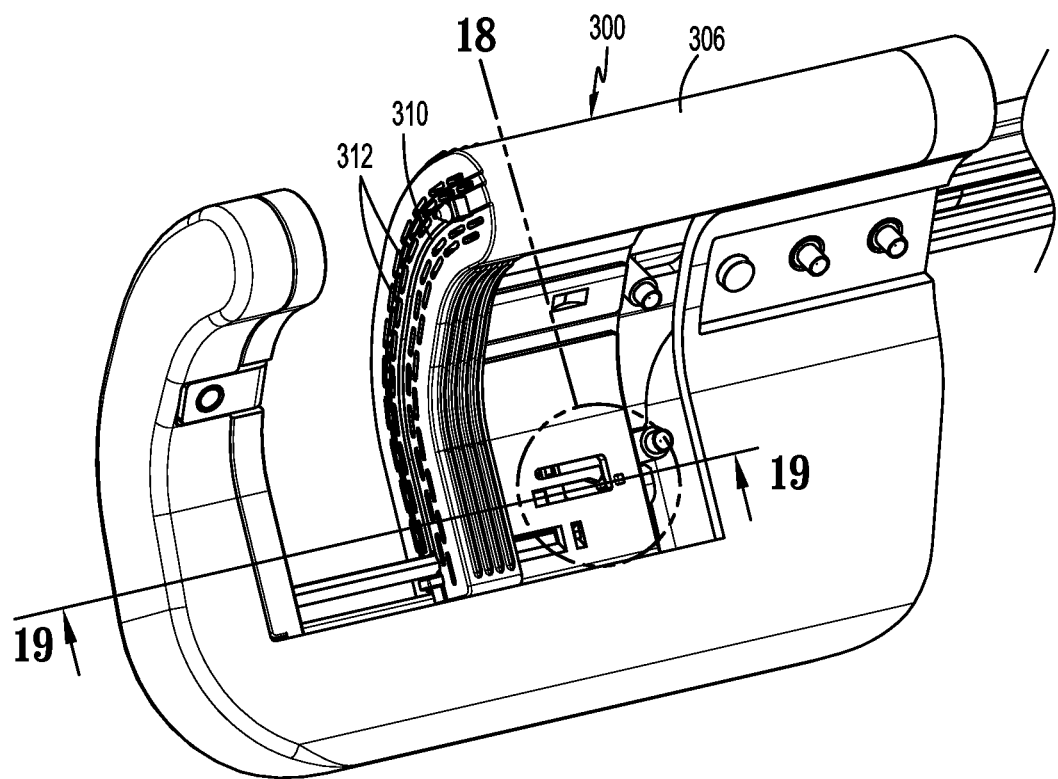
FIG. 17 is a side perspective view of the distal portion of the surgical stapling device shown in FIG. 1 including another version of a cartridge assembly supported on the stapling device with the stapling device in a retracted, unfired position.
Figure 17A:
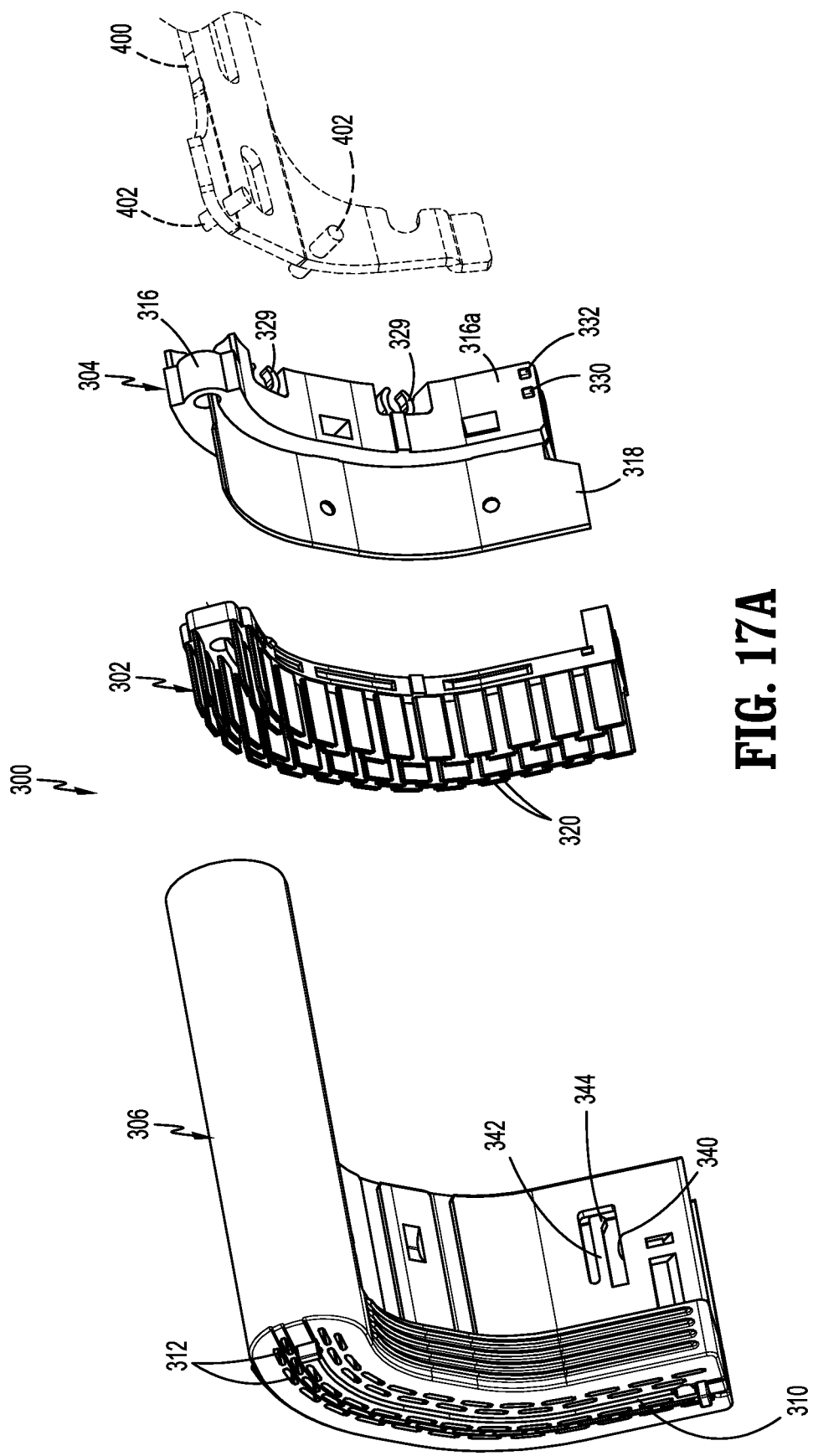
FIG. 17A is a side perspective, exploded view of the cartridge assembly shown in FIG. 17.
Figure 18:
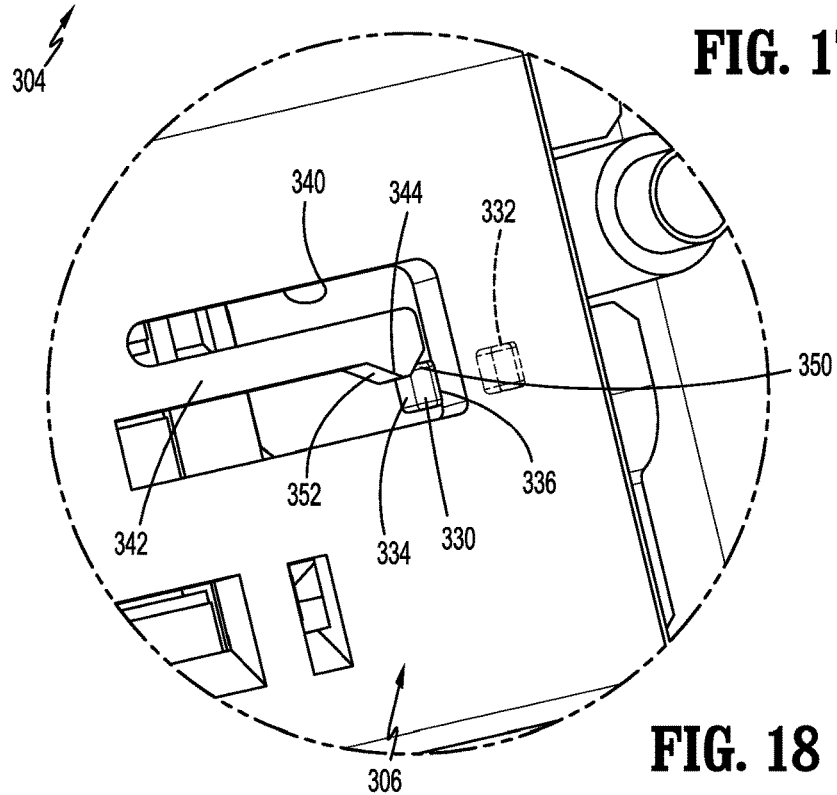
FIG. 18 is an enlarged view of the indicated area of detail shown in FIG. 17.
Figure 20:
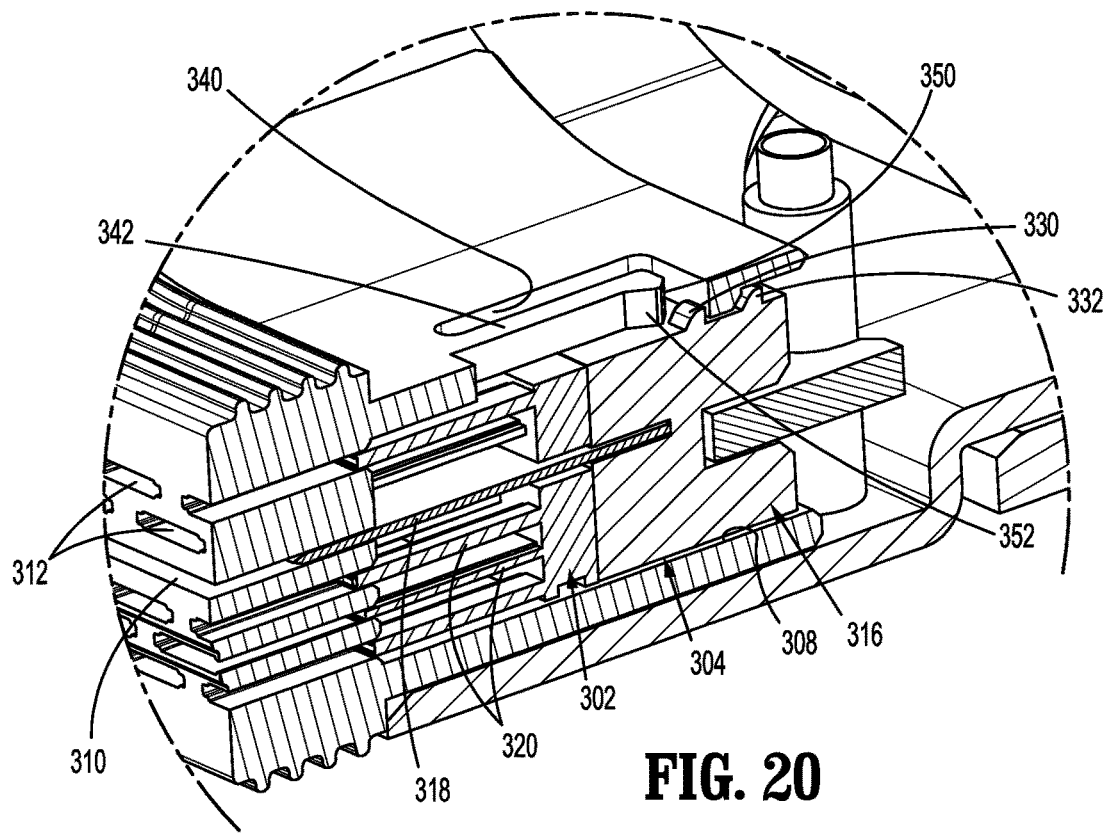
FIG. 20 is an enlarged view of the indicated area of detail shown in FIG. 19.
Figure 21:
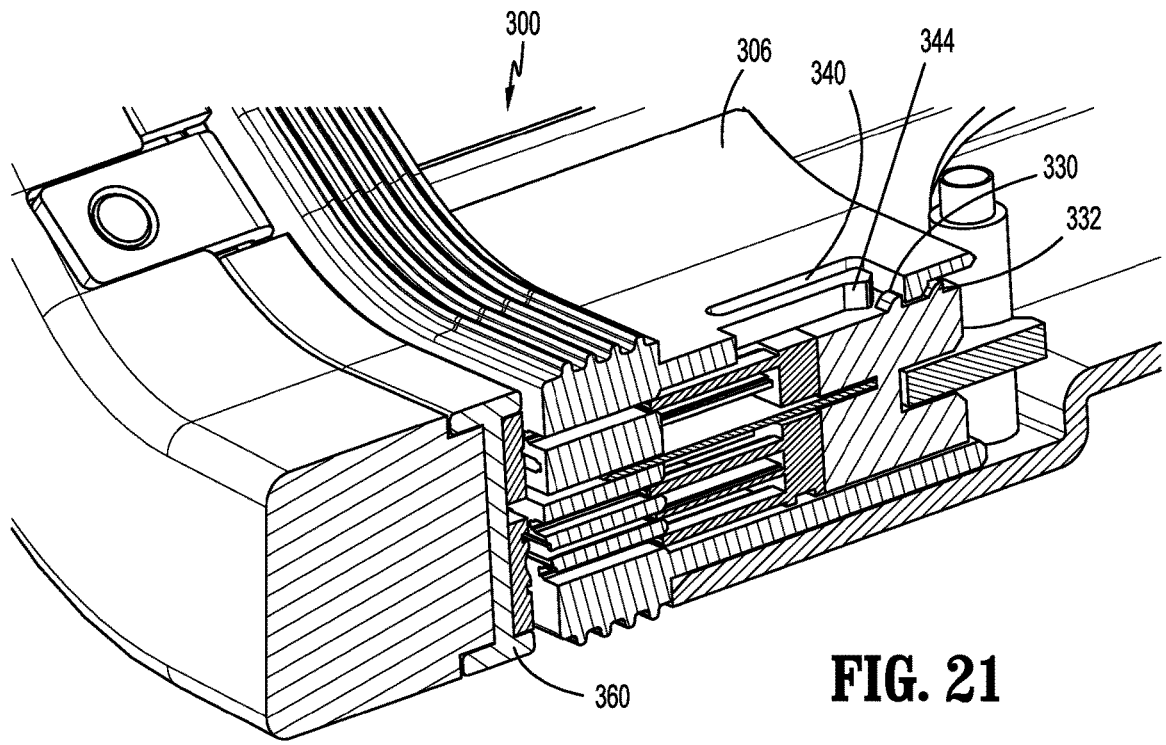
FIG. 21 is a cross-sectional view taken along section line 19-19 of FIG. 17 with the stapling device in a clamped, pre-fired position.
Figure 22:
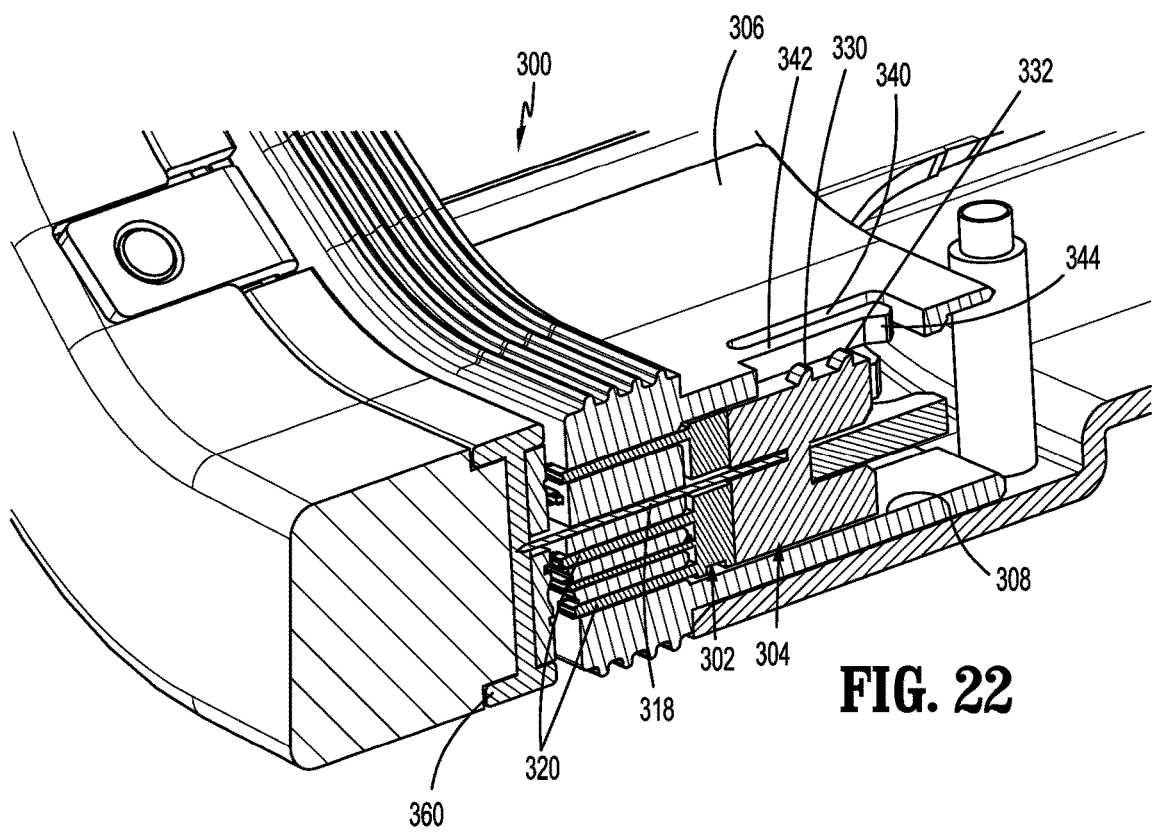
FIG. 22 is a cross-sectional view taken along section line 19-19 of FIG. 17 with the stapling device in a fired position.

FIGS. 17-23 illustrate an alternate version of the removable cartridge assembly of the stapling device 10 (FIG. 1) shown generally as cartridge assembly 300. FIGS. 17-18 illustrate the cartridge assembly 300 which includes a staple pusher 302 (FIG. 17A), a knife assembly 304 (FIG. 17A, and a cartridge body 306. The cartridge body 306 defines a cavity 308 (FIG. 20) that receives the staple pusher 302 and the knife assembly 304 for movement between retracted and advanced positions within the cavity 308. The cartridge body 306 defines a central knife slot 310 and a plurality of staple pockets 312 positioned on each side of the knife slot 310. Each of the staple pockets 312 receives a staple (not shown). The knife assembly 304 (FIG. 20) includes a knife holder 316 and a knife blade 318 that is secured to the knife holder 316. When the knife assembly 304 moves from its retracted position to its advanced position, the knife blade 318 moves from a position shielded by the cartridge body 306 (FIG. 20) to a position projecting from the cartridge body 306 through the knife slot 310 (FIG. 22). The staple pusher 302 includes fingers 320 that are aligned with the staple pockets 312. When the staple pusher 302 is moved from its retracted position to its advanced position, the fingers 320 of the staple pusher 302 move through the staple pockets 312 to eject the staples (not shown) from the cartridge body 306.

The knife holder 316 includes snap features 329 that engage posts 402 (FIG. 17A) on a thrust bar 400 to couple the knife holder 316 to the thrust bar 400 when the cartridge assembly 300 is coupled to the stapling device 10 (FIG. 1). As known in the art, the thrust bar 400 is movable between a retracted position and an advanced position to move the knife assembly 304 between its retracted and advanced positions. For a description of the operation and construction of an exemplary thrust bar, see, e.g., the '508 Patent.

The cartridge assembly 300 and the knife holder 316 include structure to retain the knife assembly 304 within the cartridge body 306 prior to firing of the cartridge assembly 300, to retain the knife assembly 304 in a retracted position after firing of the cartridge assembly 300 to prevent injury to a clinician, and to effect separation of the thrust bar 400 from the knife holder 316 upon retraction of the knife holder 316 after the stapling device 10 has been fired.

Figure 17B:
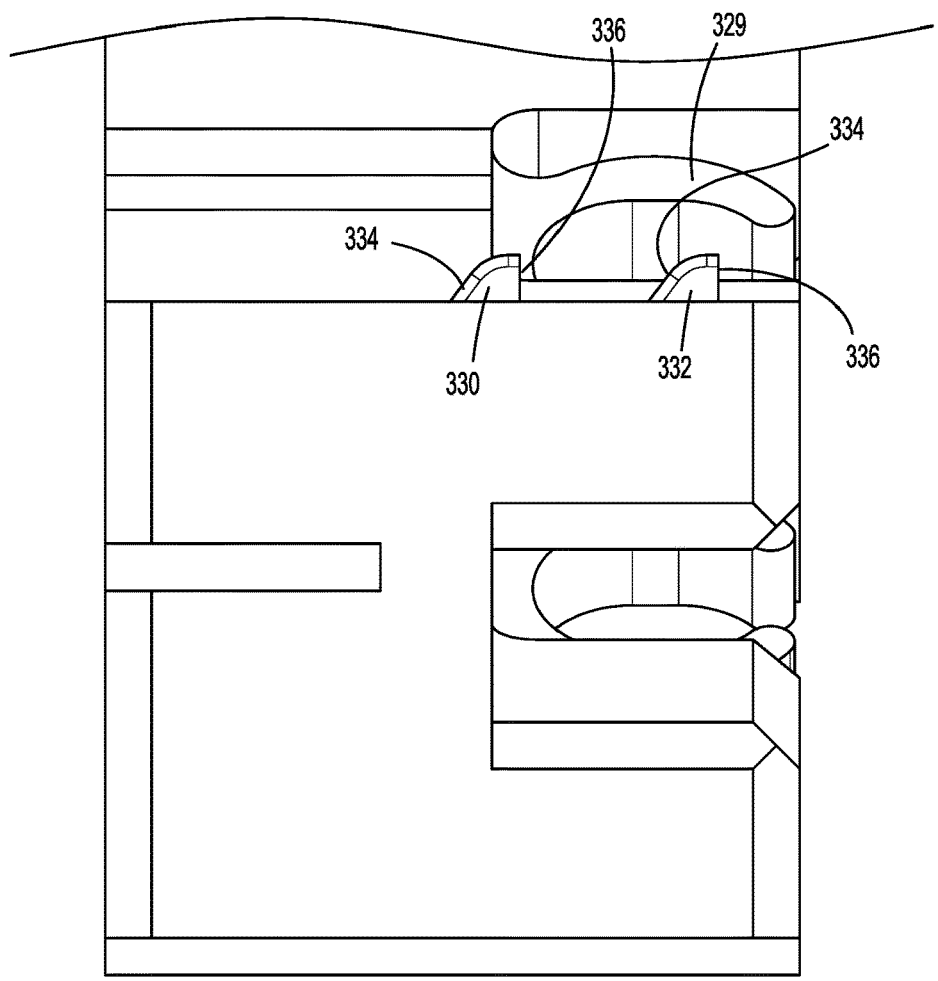
FIG. 17B is a side cutaway view of the knife holder of the cartridge assembly shown in FIG. 17.

The knife holder 316 has an outer surface 316a (FIG. 17A) including two pairs of longitudinally aligned snaps (only one is shown) including a distal snap 330 and a proximal snap 332. One pair of snaps is positioned on each side of the knife holder 316. In aspects of the disclosure, each of the distal and proximal snaps 330 and 332 (FIG. 17B) has a right-triangular configuration and includes a ramped distal surface 334 and a vertical stop surface 336.

The cartridge body 306 defines a cutout 340 and includes a resilient finger 342 that is positioned within the cutout 340. The resilient finger 342 is coupled to the cartridge body 306 at its distal end in cantilevered fashion. The proximal end of the resilient finger 342 includes a tab 344 that is aligned with the distal and proximal snaps 330 and 332 when the resilient finger 342 is in an undeformed position. The tab 344 includes tapered proximal and distal surfaces 350 and 352 (FIG. 18), respectively, that when engaged with the distal and proximal snaps 330 and 332, deform the resilient finger 342 inwardly out of the path of the distal and proximal snaps 330 and 332.

Figure 19:
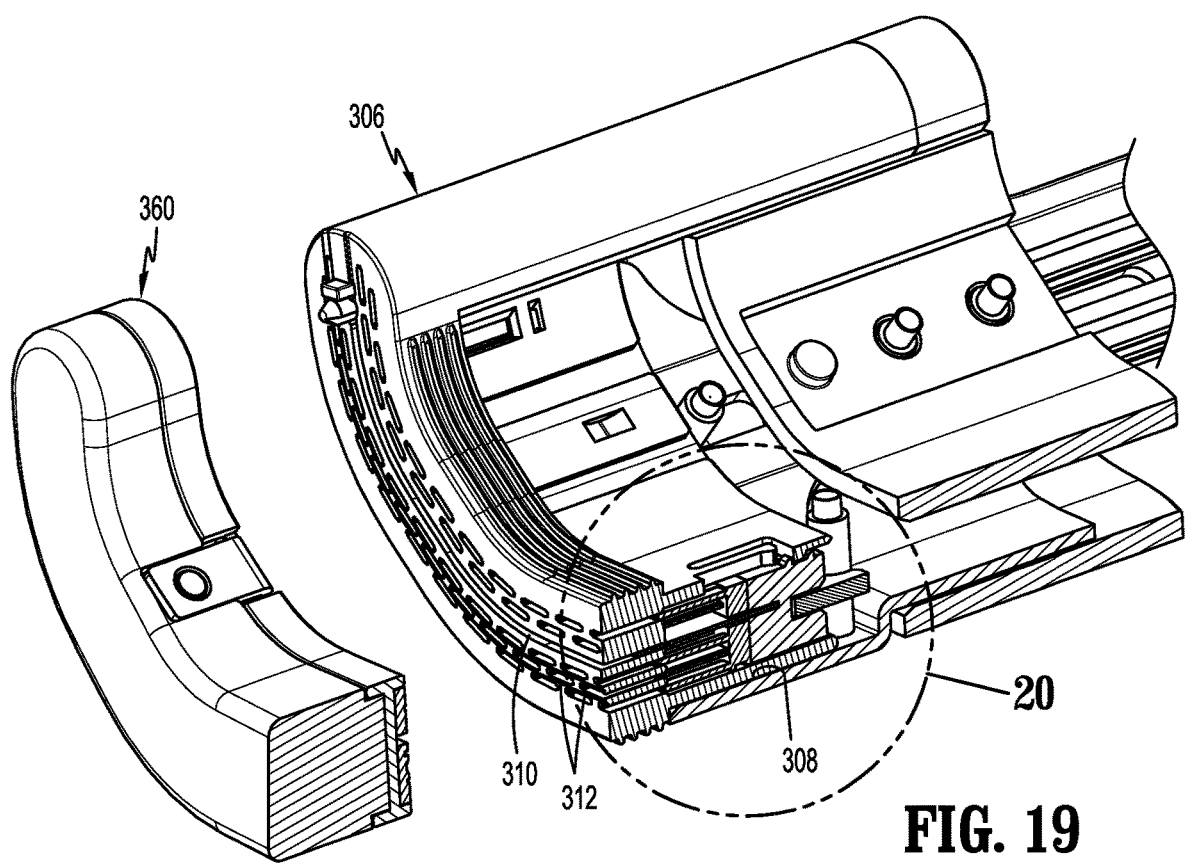
FIG. 19 is a cross-sectional view taken along section line 19-17 of FIG. 17 with the stapling device in a retracted, pre-fired position.

FIGS. 19 and 20 illustrate the tool assembly 16 of the stapling device 10 (FIG. 1) with the cartridge assembly 300 in an open position, pre-fired position. In the retracted, pre-fired position, the knife assembly 304 is positioned proximally of a staple pusher 302 within the cavity 308 of the cartridge body 306. In the pre-fired position, the distal snap 330 is received within the cutout 340 such that the stop surface 336 on the proximal side of the distal snap 330 is engaged with the cartridge body 306. Engagement between the stop surface 336 of the distal snap 330 and the cartridge body 306 obstructs proximal movement of the knife assembly 304 within the cavity 308 of the cartridge body 306 to prevent the knife assembly 304 from falling from the cavity 308 of the cartridge body 306. When the knife holder 316 is in the pre-fired retracted position, the distal surface 350 of the tab 344 on the resilient finger 342 of the cartridge body 306 is engaged with the ramped distal surface 334 of the distal snap 330 to obstruct distal movement of the knife assembly 304 within the cavity 308 of the cartridge body 306. This retains the knife blade 318 in a shielded position within the cartridge body 306.

FIG. 21 illustrates the tool assembly 16 of the stapling device 10 (FIG. 1) in the clamped position. In the clamped position, the cartridge assembly 300 is moved into approximation with an anvil assembly 360 of the tool assembly 16. The components of the cartridge assembly 300 do not change from that described above with respect to the open position. As such, no further discussion of the clamped position is included herein.

FIG. 22 illustrates the tool assembly 16 of the stapling device 10 with the cartridge assembly 300 in a clamped and fired position. In the clamped and fired positions, the staple pusher 302 and the knife assembly 304 are in their advanced positions within the cavity 308 of the cartridge body 306 with the fingers 320 of the staple pusher 302 extending through the staple pockets 312 in the cartridge body 306 and the knife blade 318 of the knife assembly 304 extending into the anvil assembly 360. In this position, the distal and proximal snaps 330 and 332 on the knife holder 316 are both positioned in the elongated cutout 340 of the cartridge body 340 distally of the tab 344 of the resilient finger 342 of the cartridge body 306. As the distal and proximal snaps 330 and 332 move distally past the tab 344 of the resilient finger 342, engagement between the snaps 330 and 332 and the tab 344 deflect the resilient finger 342 and tab 344 out of the path of the snaps 330 and 332.

Figure 23:
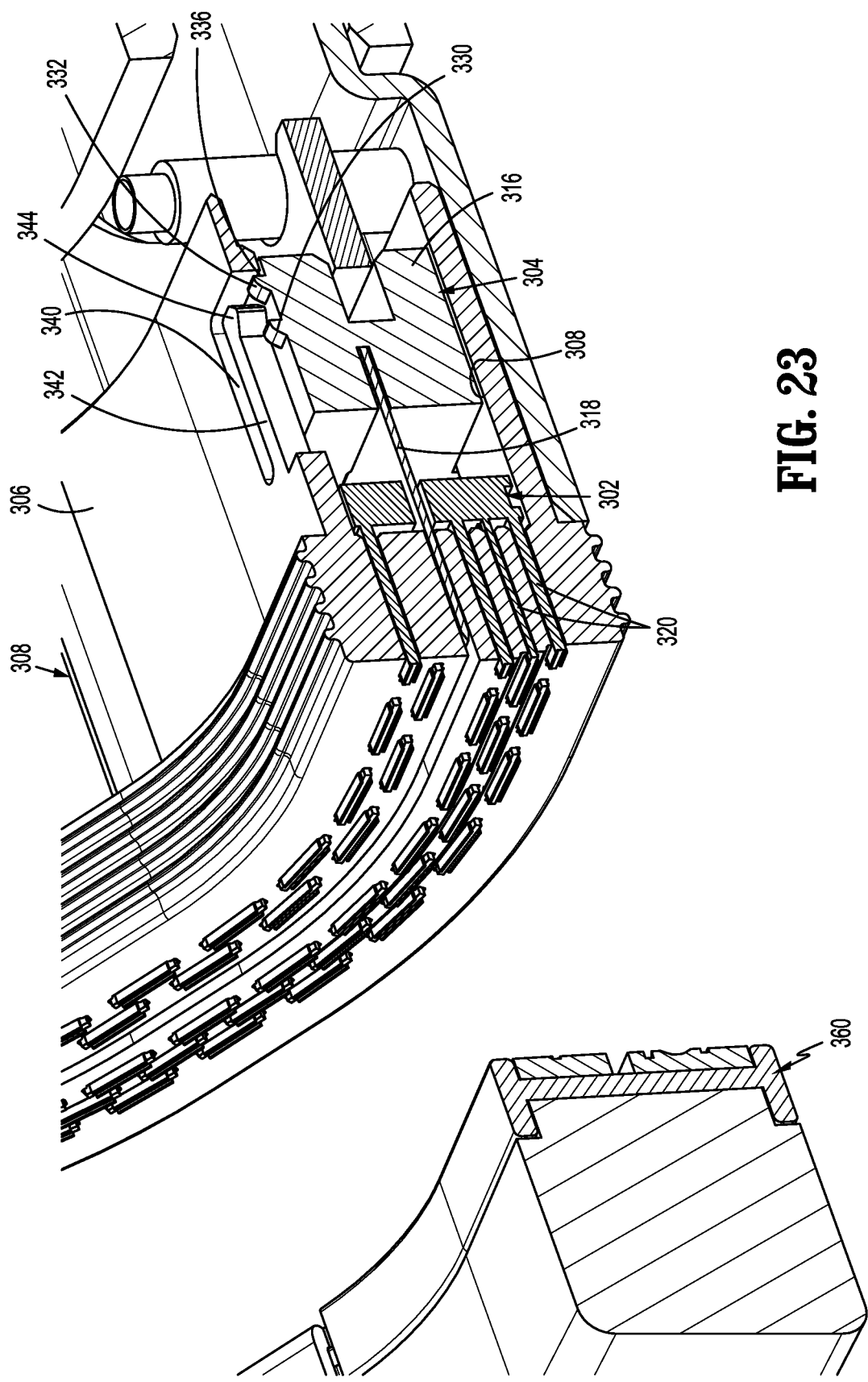
FIG. 23 is a cross-sectional view taken along section line 19-19 of FIG. 17 with the stapling device in a fired, retracted position.

FIG. 23 illustrates the tool assembly 16 of the stapling device 10 (FIG. 1) after the device 10 is fired and the cartridge assembly 300 is returned to the retracted positon. In this position, the knife assembly 304 is in its retracted position within the cavity 308 of the cartridge body 306 such that the knife blade 318 is recessed within the cartridge body 306 to protect a clinician from injury. The distal snap 330 is positioned in the cutout 340 distally of the tab 344 on the resilient finger 342 and the proximal snap 332 is positioned in the cutout 340 proximally of the tab 344. The stop surface 336 of the proximal snap 332 is engaged with the portion of the cartridge body 306 defining the cutout 340 to prevent further retraction of the knife holder 316 within the cavity 308 of the cartridge body 306. In addition, the tab 344 of the resilient finger 342 is engaged with distal surface of the proximal snap 332 to obstruct distal movement of the knife assembly 304 within the cavity 308 of the cartridge body 306 to minimize the likelihood that the knife blade 318 will move distally from the cartridge body 306 of the cartridge assembly 300 and become exposed to clinician.

It is noted that engagement of the proximal snap 332 with the cartridge body 306 prevents full retraction of the knife holder 306 with the thrust bar 400 (FIG. 17A) back to a pre-fired retracted position. As described above, in the pre-fired retracted position, the distal snap 330 is engaged with the cartridge body 306. In the post-fired retracted position, the proximal snap 332 is engaged with the cartridge body 306. As such, the knife holder 316 cannot return to its fully retracted position. Because of this, when the proximal snap 332 engages the cartridge body 306, the knife assembly 304 will be obstructed from moving proximally and the thrust bar 400 will move proximally independently of the knife holder 316. This relative movement between the thrust bar 400 (FIG. 17A) and the knife assembly 304 disengages the protrusions 402 of the thrust bar 400 from the snap features 329 of the knife holder 316 to separate the knife holder 316 from the thrust bar 400. This disengagement makes replacement of the cartridge assembly 300 easier for a clinician.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A stapling device comprising:
an elongate body having a proximal portion and a distal portion and including a clamp slide assembly and a thrust bar, the clamp slide assembly being movable from a retracted position to an advanced position and including a distal portion defining a pocket, the thrust bar having a proximal portion and a distal portion and being movable between retracted and advanced positions, the distal portion of the thrust bar including first engagement members; and
a tool assembly including:
an anvil supported on the distal portion of the elongate body, and
a cartridge assembly releasably supported within the pocket of the clamp slide assembly and being movable with the clamp slide assembly in relation to the anvil between retracted and advanced positions, the cartridge assembly including a cartridge body and a knife assembly, the cartridge body defining a cavity, a proximal cutout, and a distal cutout, the knife assembly movable within the cavity of the cartridge body between retracted and advanced positions and including a knife holder and a knife blade supported on the knife holder, the knife holder including a proximal portion including second engagement members, wherein the second engagement members are positioned to engage the first engagement members when the cartridge assembly is supported within the pocket of the clamp slide assembly to secure the knife assembly to the thrust bar, and the knife holder further including a proximal snap and a distal snap longitudinally aligned with the proximal cutout and the distal cutout, the distal snap being received within the proximal cutout when the knife assembly is in the retracted position prior to firing the stapling device to obstruct proximal movement of the knife assembly from within the cartridge body.

2. The stapling device of claim 1, wherein the first engagement members and second engagement members are snap-fit together.

3. The stapling device of claim 1, wherein the first engagement members include posts secured to the distal portion of the thrust bar and the second engagement members include C-clips secured to the knife holder of the knife assembly.

4. The stapling device of claim 3, wherein the posts have a diameter and each of the C-clips includes resilient arms that define a circular recess and an opening having a width that communicates with the circular recess, the diameter of the posts being larger than the width of the openings.

5. The stapling device of claim 3, wherein the knife holder defines a proximally facing channel and spaced cutouts positioned along the proximally facing channel, the C-clips being positioned on opposite sides of the proximally facing channel within each of the spaced cutouts.

6. The stapling device of claim 1, wherein the first engaging members include a recess formed on each of a first side and a second side of the distal portion of the thrust bar, and the second engagement members include protrusions supported on the knife holder, the protrusions received within the recesses to secure the knife holder to the thrust bar.

7. The stapling device of claim 6, wherein knife holder includes spaced resilient walls, each of the spaced resilient walls supporting one of the protrusions.

8. The stapling device of claim 7, wherein the protrusions extend into a space defined between the spaced resilient walls and the distal portion of the thrust bar is received between the spaced resilient walls.

9. The stapling device of claim 1, wherein the distal cutout has an elongated configuration.

10. The stapling device of claim 9, wherein the distal cutout receives the proximal and distal snaps when the knife assembly is in its advanced position.

11. The stapling device of claim 10, wherein the distal snap is received in the distal cutout and the proximal snap is received within the proximal cutout when the knife assembly is in the retracted position after firing of the stapling device, receipt of the proximal snap within the proximal cutout obstructing distal movement of the knife assembly within the cavity of the cartridge body.

12. The stapling device of claim 11, wherein the proximal snap has a triangular configuration and includes proximal and distal ramped surfaces, and the distal snap has a right-triangular configuration and includes a distal ramped surface and a proximal stop surface.

13. The stapling device of claim 1, further including a handle assembly having a stationary handle and a trigger that is movable in relation to the stationary handle to move the thrust bar between its retracted and advanced positions and move the clamp slide assembly between its retracted and advanced positions.

14. The stapling device of claim 1, wherein the distal snap is positioned to engage a portion of the cartridge body defining the distal cutout after firing of the stapling device prior to movement of the thrust bar to its retracted position such that the thrust bar moves to its retracted position independently of the knife holder, the movement of thrust bar independently of the knife holder effecting separation of the first and second engagement members to disengage the thrust bar from the knife holder.

15. A cartridge assembly comprising:
a cartridge body defining a cavity and at least one cutout; and
a knife assembly movable within the cavity of the cartridge body between retracted and advanced positions, the knife assembly including a knife holder and a knife blade supported on the knife holder, the knife holder including a proximal snap and a distal snap that are longitudinally aligned with each other and with the at least one cutout in the cartridge body, the distal and proximal snaps having a triangular configuration and including distal ramped surfaces, the distal snap received within the at least cutout and engaging the cartridge body when the knife assembly is in a pre-fired retracted position to obstruct proximal movement of the knife assembly from within the cartridge body and the proximal snap positioned within the at least one cutout and engaging the cartridge body when the knife holder is in a post-fired retracted position to obstruct proximal movement of the knife assembly.

16. The cartridge assembly of claim 15, wherein the at least one cutout includes an elongated configuration, the at least one cutout receiving the proximal and distal snaps when the knife assembly is in its advanced position.

17. The cartridge assembly of claim 16, wherein the at least one cutout includes a proximal cutout and a distal cutout, the distal cutout having the elongated configuration, the distal snap being received in the distal cutout and the proximal snap being received within the proximal cutout when the knife assembly is in the post-fired retracted position, receipt of the proximal snap within the proximal cutout obstructing distal movement of the knife assembly within the cavity of the cartridge body.

18. A stapling device comprising:
an elongate body having a proximal portion and a distal portion and including a clamp slide assembly and a thrust bar, the clamp slide assembly being movable from a retracted position to an advanced position and including a distal portion defining a pocket, the thrust bar having a proximal portion and a distal portion and being movable between retracted and advanced positions, the distal portion of the thrust bar including first engagement members; and
a tool assembly including:
an anvil supported on the distal portion of the elongate body, and
a cartridge assembly releasably supported within the pocket of the clamp slide assembly and being movable with the clamp slide assembly in relation to the anvil between retracted and advanced positions, the cartridge assembly including a cartridge body and a knife assembly, the cartridge body defining a cavity, a proximal cutout, and a distal cutout, the proximal cutout and the distal cutout being longitudinally aligned with each other, the distal cutout having an elongated configuration, the knife assembly movable within the cavity of the cartridge body between retracted and advanced positions and including a knife holder and a knife blade supported on the knife holder, the knife holder including a proximal portion including second engagement members, wherein the second engagement members are positioned to engage the first engagement members when the cartridge assembly is supported within the pocket of the clamp slide assembly to secure the knife assembly to the thrust bar, the knife holder further including a proximal snap and a distal snap that are longitudinally aligned with each other and with the proximal and distal cutouts in the cartridge body, the proximal snap having a triangular configuration and including proximal and distal ramped surfaces, and the distal snap having a right-triangular configuration and including a distal ramped surface and a proximal stop surface, the distal snap being received within the proximal cutout when the knife assembly is in the retracted position prior to firing of the stapling device to obstruct proximal movement of the knife assembly from within the cartridge body.

19. The stapling device of claim 18, further including a handle assembly having a stationary handle and a trigger that is movable in relation to the stationary handle to move the thrust bar between its retracted and advanced positions and move the clamp slide assembly between its retracted and advanced positions.

* * * * *